(12) United States Patent
Manabe et al.

(10) Patent No.: US 11,160,691 B2
(45) Date of Patent: Nov. 2, 2021

(54) ABSORBENT ARTICLE WITH STRONG AND WEAK BONDED PORTIONS

(71) Applicant: DAIO PAPER CORPORATION, Ehime (JP)

(72) Inventors: Sadanao Manabe, Tokyo (JP); Ryoichi Ochi, Ehime (JP); Yosuke Mori, Ehime (JP); Yohei Ono, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 589 days.

(21) Appl. No.: 16/088,879

(22) PCT Filed: Feb. 23, 2017

(86) PCT No.: PCT/JP2017/006712
§ 371 (c)(1),
(2) Date: Sep. 27, 2018

(87) PCT Pub. No.: WO2017/169342
PCT Pub. Date: Oct. 5, 2017

(65) Prior Publication Data
US 2019/0110934 A1    Apr. 18, 2019

(30) Foreign Application Priority Data
Mar. 30, 2016    (JP) .............................. JP2016-069157

(51) Int. Cl.
*A61F 13/15*    (2006.01)
*A61F 13/532*    (2006.01)
(Continued)

(52) U.S. Cl.
CPC ........ *A61F 13/15203* (2013.01); *A61F 13/49* (2013.01); *A61F 13/532* (2013.01);
(Continued)

(58) Field of Classification Search
CPC .. A61F 13/15203; A61F 13/49; A61F 13/532; A61F 13/5323; A61F 13/533;
(Continued)

(56) References Cited

U.S. PATENT DOCUMENTS 5,433,715 A    7/1995    Tanzer et al.
5,994,614 A    11/1999    Wada et al.
(Continued)

FOREIGN PATENT DOCUMENTS

JP    1997-504207 A    4/1997
JP    1997-327479 A    12/1997
(Continued)

OTHER PUBLICATIONS

International Search Report for PCT/JP2017/006712, dated May 16, 2017.

*Primary Examiner* — Michele M Kidwell
(74) *Attorney, Agent, or Firm* — Andrus Intellectual Property Law, LLP

(57) ABSTRACT

An absorbent article includes an absorber including cells, each of which is surrounded by bonded portions of a front surface side sheet and a back surface side sheet and in each of which the front surface side sheet and the back surface side seat are not bonded, and including superabsorbent polymer particles contained in each of the cells. The bonded portions are arranged in dotted line shapes according to a pattern in which same-sized octagonal portions having all interior angles of 135°, and having two pairs of opposite sides whose facing directions are mutually orthogonal are equal in length, and diamond-shaped portions each having equal length of all sides and being formed in portions among the octagonal portions, are arranged without any space in the front-back direction (LD) or the width direction (WD).

12 Claims, 17 Drawing Sheets

(51) Int. Cl.
*A61F 13/533* (2006.01)
*A61F 13/535* (2006.01)
*A61F 13/537* (2006.01)
*A61F 13/53* (2006.01)
*A61F 13/49* (2006.01)
*A61F 13/56* (2006.01)
*A61F 13/539* (2006.01)

(52) U.S. Cl.
CPC .......... *A61F 13/533* (2013.01); *A61F 13/535* (2013.01); *A61F 13/5616* (2013.01); *A61F 13/53747* (2013.01); *A61F 2013/15406* (2013.01); *A61F 2013/15422* (2013.01); *A61F 2013/15463* (2013.01); *A61F 2013/15544* (2013.01); *A61F 2013/53035* (2013.01); *A61F 2013/530051* (2013.01); *A61F 2013/530299* (2013.01); *A61F 2013/53908* (2013.01)

(58) Field of Classification Search
CPC .............. A61F 13/535; A61F 13/53747; A61F 13/5616; A61F 2013/15406; A61F 2013/15422; A61F 2013/15463; A61F 2013/15544; A61F 2013/530051; A61F 2013/530299; A61F 2013/53035; A61F 2013/53908
See application file for complete search history.

(56) References Cited

U.S. PATENT DOCUMENTS

| | | | |
|---|---|---|---|
| 9,066,835 B2* | 6/2015 | Okawa | A61F 13/505 |
| 9,532,909 B2* | 1/2017 | Umebayashi | B29C 66/73921 |
| 10,813,800 B2* | 10/2020 | Konawa | A61F 13/533 |
| 2004/0253892 A1* | 12/2004 | Baker | A61F 13/15731 |
| | | | 442/327 |
| 2015/0038929 A1 | 2/2015 | Van Malderen | |
| 2015/0148766 A1 | 5/2015 | Nakakado | |
| 2016/0151213 A1* | 6/2016 | Bauduin | A61L 15/58 |
| | | | 604/365 |
| 2016/0250083 A1* | 9/2016 | Tsujimoto | A61F 13/15739 |
| | | | 604/385.01 |
| 2018/0042782 A1* | 2/2018 | Konawa | A61F 13/15 |
| 2019/0125596 A1* | 5/2019 | Manabe | A61F 13/533 |

FOREIGN PATENT DOCUMENTS

| | | |
|---|---|---|
| JP | 1998-137291 A | 5/1998 |
| JP | 2003-265525 A | 9/2003 |
| JP | 2009-061230 A | 3/2009 |
| JP | 2011-189067 A | 9/2011 |
| JP | 0003172565 U | 12/2011 |
| JP | 2014-500736 A | 1/2014 |
| WO | 2012/118235 | 9/2012 |

* cited by examiner (a)

(b)

(a)

(b)

ABSORBENT ARTICLE WITH STRONG AND WEAK BONDED PORTIONS

CROSS-REFERENCE TO RELATED APPLICATIONS

This application is the U.S. national stage application of International Application PCT/JP2017/006712, filed Feb. 23, 2017, which international application was published on Oct. 5, 2017, as International Publication WO 2017/169342 in the Japanese language. The International Application claims priority of Japanese Patent Application No. 2016-069157, filed Mar. 30, 2016. The international application and Japanese application are both incorporated herein by reference, in entirety.

TECHNICAL FIELD

The present invention relates to an absorbent article such as a disposable diaper and a sanitary napkin.

BACKGROUND ART

The absorbent article includes an absorber and a liquid-pervious top sheet covering the front surface side of the absorber. Excretion liquid such as urine and menstrual blood passes through the top sheet and is absorbed and held by the absorber. An absorber obtained by mixing superabsorbent polymer (SAP) particles with hydrophilic short fibers such as fluff pulp and being accumulated in a cotton form has been widely used. However, in response to the request for further thinning, weight reduction, and cost reduction while ensuring a sufficient absorbable amount, various types of absorbers (hereinafter also referred to as cell absorbers) are proposed which include a large number of cells (small chambers), which are surrounded by bonded portions of the front surface side sheet and the back surface side sheet and in which the front surface side sheet and the back surface side sheet are not bonded, and include particulate materials containing superabsorbent polymer particles included in the cells (for example, refer to Patent Literatures 1 to 8 below).

In such a cell absorber, when the volume of the superabsorbent polymer particles in the state of saturated absorption in each cell is sufficiently larger than the volume of the cell, the superabsorbent polymer particles fill in the cell upon the absorption, and there is a possibility that the absorption amount and absorption rate are lowered due to inhibition by the swelling and so-called gel blocking, the comfort in wearing may be deteriorated since the cell becomes hard due to the swelling pressure of the superabsorbent polymer particles, and the superabsorbent polymer particles may leak from gaps among fibers in the case where the front surface side sheet and the back surface side sheet are nonwoven fabrics.

For this reason, in the cell absorber, a structure is proposed in which the bonded portions of the front surface side sheet and the back surface side sheet are peeled off during absorption, and the volume of each cell is enlarged by coalescence of adjacent cells (for example, refer to Patent Ligatures 1 to 5 below).

However, the conventional cell absorber has room for improvement in terms of ease of coalescence of adjacent cells (that is, ease of peeling off of the bonded portions between the adjacent cells) and increase in the volume of the cell relative to the number of coalesced cells.

CITATION LIST

Patent Literature

Patent Literature 1: JP 2009-061230 A
Patent Literature 2: JP 09-504207 A
Patent Literature 3: JP 2014-500736 A
Patent Literature 4: Registered Utility Model No. 03172565
Patent Literature 5: JP 2011-189067 A
Patent Literature 6: JP 09-327479 A
Patent Literature 7: JP 10-137291 A
Patent Literature 8: JP 2003-265525 A

SUMMARY OF INVENTION

Technical Problem

Therefore, an object of the present invention is to provide an absorbent article having a cell absorber in which adjacent cells can be easily coalesced and which is excellent in the amount of increase in the volume of the cell relative to the number of coalesced cells.

Solution to Problem

Representative aspects of the present invention that solve the above problems are as follows.
<First Aspect>
An absorbent article comprising an absorber including:
a front surface side sheet;
a back surface side sheet disposed on the back surface side of the front surface side sheet;
a plurality of cells each of which is surrounded by bonded portions of the front surface side sheet and the back surface side sheet and inside each of which the front surface side sheet and the back surface side sheet are not bonded; and
particulate materials which include superabsorbent polymer particles and which are contained in each of the cells,
wherein the same-sized octagons in which all interior angles are 135°, and the lengths of two pairs of opposite sides whose facing directions are mutually orthogonal are equal are arranged without space in the front-back direction and the width direction,
along the pattern in which a portion between the octagonal portions forms a diamond shape whose length of all sides are equal,
the bonded portions are provided in a continuous line shape or a dotted line shape,
as the cells, octagonal cells surrounded by the octagonal portions of the bonded portions and diamond-shaped cells surrounded by the diamond-shaped portions of the bonded portions are included, and
the bonded portions positioned on at least continuous two sides in each of the octagonal cells are weak bonded portions which can be peeled off due to the swelling force of the superabsorbent polymer particles in the cells adjacent to the bonded portions.
(Function and Effect)
In the pattern of the present invention, each side of the diamond shape is common to the side in the oblique direction of the octagon, and the octagons, which are adjacent to each other in the front-back direction and the octagons, which are adjacent to each other in the width direction, have the adjacent sides in common, such that, due to the swelling pressure in the octagonal cells, the peeling force is applied to both the bonded portions which are common and the bonded portions which are non-common to those of the side of the adjacent diamond shape. Comparing with other shapes with the same cell area, octagonal cells, each having all eight interior angles of 135°, and having two pairs of opposite sides whose facing directions are mutually orthogonal, have relatively short circumferential lengths. Therefore, in the case where the bonded portions surrounding the cell can be peeled off due to the swelling of the superabsorbent polymer particles in the cell, the bonded portions can be peeled off with the weak swelling force. Therefore, when the bonded portions and the cells are provided according to the pattern of the present invention, the adjacent cells are coalesced more smoothly and rapidly upon the absorption. In addition, if the bonded portions positioned at least on continuous two sides in each octagonal cell are the weak bonded portions, the increase in the volume of the cell relative to the number of the coalesced cells is also excellent. Therefore, it is possible to efficiently increase the volume due to the coalescence of the cells.

<Second Aspect>

The absorbent article according to the first aspect, wherein the diamond-shaped cell does not contain a superabsorbent polymer particle or contains a smaller amount of the superabsorbent polymer particles per unit area than the orthogonal cells.

(Function and Effect)

Since the diamond-shaped cell has a relatively smaller volume than the octagonal cell, in the case where the contained amount of the superabsorbent polymer particles per unit area is the same, when the superabsorbent polymer particles are swollen upon the absorption, the diamond-shaped cells are filled first, and the bonded portions in the oblique direction in the bonded portions surrounding the octagonal cells are first peeled off, and the direct coalescence of the octagonal cells is delayed. To enhance the increase in the volume of the cell relative to the number of coalesced cells, it is desirable that the diamond-shaped cells do not contain the superabsorbent polymer particles or contains a smaller amount of the superabsorbent polymer particles per unit area than the octagonal cells.

<Third Aspect>

The absorbent article according to the first or second aspect, wherein, in the bonded portions provided in the octagonal patterns, first bonded portions positioned on the sides along the front-back direction and the width direction have lower bonding strength than second bonded portions positioned on the sides along the oblique direction, and the first bonded portions are peeled off more preferentially than the second bonded portions by the swelling force of the superabsorbent polymer particles.

(Function and Effect)

When the bonded portions are peeled off with such a priority order, the first bonded portions are peeled off at the initial stage, and the octagonal cells are coalesced vertically and horizontally to form large coalesced cells immediately. In addition, since the diamond-shaped cells are depressed low until the second bonded portions are peeled off, the contact area with the skin can be reduced.

<Fourth Aspect>

The absorbent article according to the first or second aspect, wherein, in the bonded portions provided in the octagonal patterns, first bonded portions positioned on the sides along the front-back direction and the width direction have higher bonding strength than second bonded portions positioned on the sides along the oblique direction, and the second bonded portions are peeled off more preferentially than the first bonded portion by the swelling force of the superabsorbent polymer particles.

(Function and Effect)

When the bonded portions are peeled off with such a priority order, the second bonded portions are peeled off at the initial stage, and the octagonal cells are coalesced in the oblique direction to form large coalesced cells immediately. In addition, since the first bonded portions can suppress an increase in the thickness of the absorber until the first bonded portions are peeled off, it is possible to prevent a local increase in the thickness of the absorber at portions that have absorbed liquid.

<Fifth Aspect>

The absorbent article according to the first or second aspect, comprising a plurality of maximum enlargement sections in each of which a portion where three or more octagonal cells and four or more diamond-shaped cells are arranged respectively without any space in the front-back direction and the width direction is surrounded by strong bonded portions which are not peeled off against the swelling force of the superabsorbent polymer particles in the adjacent cells, wherein the bonded portions positioned inside the strong bonded portions in the maximum enlargement sections, are the weak bonded portions.

(Function and Effect)

If the bonded portions are uniformly peeled off almost entirely except for the peripheral edge of the cell absorber as in the conventional cases, the gelled superabsorbent polymer particles swollen upon the absorption move and collect to a low place such as a crotch portion, and the comfort in the wearing may be deteriorated.

On the other hand, as described in Patent Literature 3, it is effective that a large number of strong bonded portions which are not peeled off upon the absorption and a large number of weak bonded portions which are peeled off upon the absorption are combined, the weak bonded portions are provided at intervals in maximum enlargement sections surrounded by the strong bonded portions, respectively and superabsorbent polymer particles are arranged in the cells surrounded by these bonded portions, respectively. However, as illustrated in FIG. 5 of Patent Literature 3, if the maximum enlargement section surrounded by the strong bonded portions is too small, it becomes insignificant to provide the strong bonded portions, and as illustrated in FIG. 14, when the maximum enlargement section is formed to be elongated, after the cells are coalesced, the maximum enlargement section becomes to have a shape in which it is difficult for the cells to be swollen.

On the contrary, when the strong bonded portions surround the portion composed of three or more octagonal cells and four or more diamond-shaped cells arranged without any space in the front-back direction and the width direction to form the maximum enlargement section, the cells are successively coalesced and smoothly enlarged to the maximum enlargement section, and the maximum enlargement section has a shape that is easy to be swollen, and the increase in the volume of the cell relative to the number of the coalesced cells is excellent when the cells are enlarged to the maximum enlargement section.

<Sixth Aspect>

The absorbent article according to the fifth aspect, wherein longitudinal-strong-bond lines on which the strong bonded portions are continuously or intermittently provided in the front-back direction along the maximum length of the absorber, are provided in the center portion and the both side portions in the width direction of the absorber, respectively, a plurality of lateral-strong-bond lines on which the strong bonded portions are continuously or intermittently provided in the width direction or the oblique direction from the longitudinal-strong-bond line in the center portion to each of the longitudinal-strong-bond lines in the both side portions is provided at intervals in the front-back direction, and sections, which are surrounded by the longitudinal-strong-bond lines and the lateral-strong-bond lines so as to be partitioned, are the maximum enlargement sections.

(Function and Effect)

The strong bonded portions are not peeled off even if the cells on the both sides thereof are swollen upon the absorption, and a groove having the strong bonded portions as the bottom is formed after the absorption. Therefore, the liquid diffusibility in the direction along the groove improves. Therefore, in the case of this aspect, the liquid diffusibility in the longitudinal direction is improved by the longitudinal-strong-bond lines in each of which the strong bonded portions are continuously arranged in the front-back direction, and the liquid diffusibility in the lateral direction is improved by the lateral-strong-bond line in each of which the strong bonded portions are continuously arranged in the width direction or oblique direction. In addition, the longitudinal-strong-bond lines in the both side portions also have a function of preventing leakage of the superabsorbent polymer particles from the both side edges.

<Seventh Aspect>

The absorbent article according to the sixth aspect, wherein the lateral-strong-bond lines are formed in a zigzag shape extending in the front-back direction while repeatedly bending left and right between the longitudinal-strong-bond line in the center portion and each of the longitudinal-strong-bond lines in the both side portions.

(Function and Effect)

When the lateral-strong-bond lines are formed in a zigzag shape as described above, it is preferable, because liquid diffusion in the lateral direction can be efficiently facilitated with the small number of the lateral-strong-bond lines, each maximum enlargement section has a substantially triangular shape which is easily swollen, and the increase in the volume of the cell relative to the number of coalesced cells is excellent.

<Eighth Aspect>

The absorbent article according to any one of the fifth to seventh aspects, wherein the bonded portions are portions where the front surface side sheet and the back surface side sheet are welded, the weak bonded portions and the strong bonded portions are provided in dotted line patterns, the line width of the weak bonded portions is narrower than the line width of the strong bonded portions, and the point interval of the weak bonded portions is wider than the point interval of the strong bonded portions (Function and Effect)

In the case of forming the bonded portions by welding the front surface side sheet and the back surface side sheet, the weak bonded portions can be formed only by forming the bonded portions into a dotted line shape and widening the point interval. However, since the bonded portions function as a boundary between each pair of the adjacent cells, if the point interval becomes too large, the gaps are increased in the boundary between each pair of the adjacent cells, which causes the superabsorbent polymer particles to move easily. Therefore, when the weak bonded portions are formed into a dotted line shape by while the line width of the bonded portions and the interval of each pair of the adjacent bonded portions are arranged in combination, the weak bonded portions are likely to be peeled off in spite of the narrow gaps.

<Ninth Aspect>

The absorbent article according to any one of the first to eighth aspects, wherein at least one low-swelling-cell row in which all of the bonded portions of the both side edges thereof aligned linearly in the front-back direction are the strong bonded portions is provided in the center in the width direction of the absorber, and the both sides in the width direction of the low-swelling-cell row, have a higher swellable height than the low-swelling-cell row.

(Function and Effect)

The low-swelling-cell row is a row in which both side edges comprised of the strong bonded portions are aligned linearly in the front-back direction and the maximum volume is small, and the height can be kept low even if the inside superabsorbent polymer particles are swollen. When the portions having a higher swellable height than the low-swelling-cell row are provided on the both sides in the width direction of the low-swelling-cell row, a groove having the low-swelling-cell row as the bottom is formed after the absorption, and therefore the liquid diffusibility in the front-back direction along the groove improves.

<Tenth Aspect>

The absorbent article according to any one of the first to ninth aspects, wherein the bonded portion is not provided at positions where the sides on which the weak bonded portions are positioned intersect with each other in the cells.

(Function and Effect)

If the bonded portion is not provided at the positions where the sides on which the weak bonded portions are positioned intersect with each other, it is preferable since the weak bonded portions are likely to be peeled off, and the cells are coalesced smoothly.

<Eleventh Aspect>

The absorbent article according to any one of the first to tenth aspects, wherein at least cells provided at positions through which the front and back ends of the absorber pass and cells in the both side portions in an intermediate portion of the front-back direction of the absorber are empty cells which do not contain a superabsorbent polymer particle or which contains a smaller amount of the superabsorbent polymer particles per unit area than other cells.

(Function and Effect)

For example, since the front end and the back end of the absorber are formed by cutting into individual absorbers in the manufacturing, if the superabsorbent polymer particles are included in the front end and the back end of the absorber, the life of a blade of a cutting device may be shortened. Therefore, it is desirable that the cells at the positions through which the front and back ends of the absorber pass be empty cells. Further, in the absorber obtained by mixing the superabsorbent polymer particles with hydrophilic short fibers such as fluff pulp and accumulating them in a cotton form, generally the intermediate portion of the absorber in the front-back direction LD is formed in a shape narrowing along the legs. However, even in the cell absorber, by setting the cells on the both side portions in the intermediate portion in the front-back direction as the empty cells, this portion is less swollen even after absorption, and therefore, the absorber fits around the legs even after the absorption.

Advantage Effects of Invention

The present invention provides an advantage that an absorbent article having a cell absorber in which adjacent cells can be easily coalesced and which is excellent in the increase in the volume of the cell with respect to the number of cell coalescence.

DESCRIPTION OF EMBODIMENTS

Figure 1:
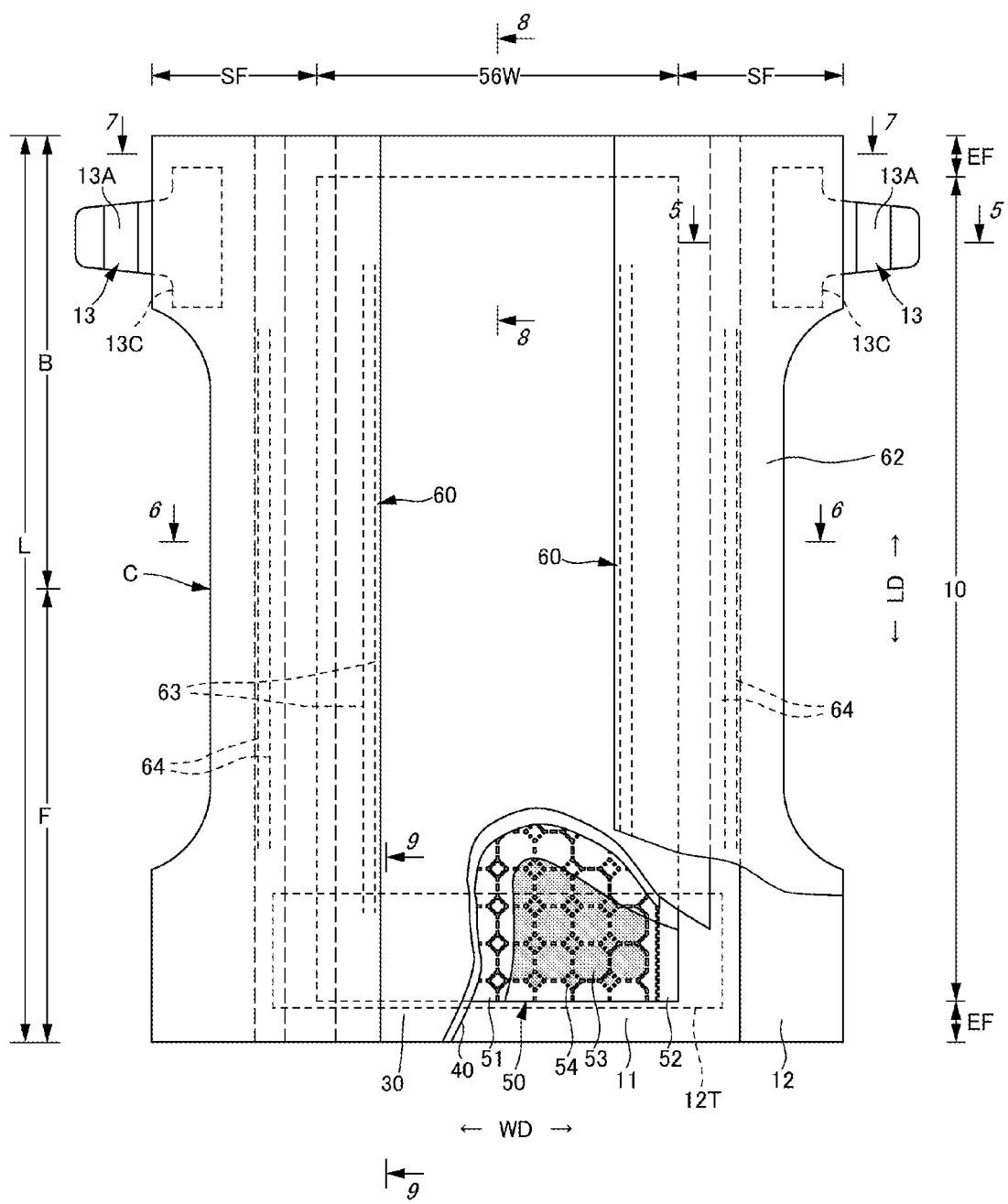
FIG. 1 is a plan view illustrating the inner surface of a tape-type disposable diaper in a state where a diaper is spread.

Hereinafter, embodiments of the present invention will be described with reference to the accompanying drawings.
<Example of Absorbent Article>

FIGS. 1 to 6 illustrate examples of a tape-type disposable diaper, in which the reference sign X indicates the maximum width of the diaper excluding a fastening tape, and the reference sign L indicates the maximum length of the diaper. Each component member is fixed or bonded in the same manner as known diapers as necessary except for the fixing or bonded portion described below. As a unit for fixing or bonding, a hot melt adhesive or welding (heat welding, ultrasonic welding) can be selected as appropriate.

This tape type disposable diaper has a basic structure in which an absorber 50 is interposed between a liquid pervious top sheet and a liquid impervious sheet positioned on the external surface side. The tape type disposable diaper includes a ventral side end flap portion EF, a dorsal side end flap portion EF, and a pair of side flap portions SF. The ventral side end flap portion EF and the dorsal side end flap portion EF are portions extending to the front side and the back side of the absorber 50 respectively and do not include the absorber 50. The pair of the side flap portions SF extends laterally from the side edges of the absorber 50. In each of the side flap portions SF in a dorsal side portion B, a fastening tape 13 is provided. When a user wears the diaper, the fastening tape 13 is engaged at an appropriate place on the external surface of the ventral side portion F in a state in which the side flap portion SF of the dorsal side portion B is overlaid on the external side of the side flap portion SF of the ventral side portion F.

In this tape type disposable diaper, the entire external surface of the absorbent main unit 10 and the side flap portions SF is formed by an outer sheet 12. Particularly, in a region including the absorber 50, a liquid impervious sheet 11 is fixed to the internal surface side of the outer sheet 12 with an adhesive such as a hot melt adhesive. Further, the absorber 50, an intermediate sheet 40, and a top sheet 30 are stacked in this order on the internal surface side of the liquid impervious sheet 11. In the illustrated example, the top sheet 30 and the liquid impervious sheet 11 are rectangular in shape and have somewhat larger sizes in the front-back direction LD and the width direction WD than the absorber 50. The peripheral edge portion protruding from the side edges of the absorber 50 in the top sheet 30 and the peripheral edge portion protruding from the side edges of the absorber 50 in the liquid impervious sheet 11 are bonded by a hot melt adhesive or the like. Further, the liquid impervious sheet 11 is formed to be slightly wider than the top sheet 30.

On both sides of the absorbent main unit 10, three-dimensional side gathers 60 and 60 projecting (standing) to the skin side of a wearer are provided, and gather sheets 62 and 62 forming the three-dimensional side gathers 60 and 60 are fixed in a range from the upper both sides of the top sheet 30 to the inner surfaces of the side flap portions SF.

Details of each part will be described in order below.
(Outer Sheet)

The outer sheet 12 is a sheet constituting the external surface of a product. The outer sheet 12 has a shape in which the intermediate portions in the front-back direction LD on the both side portions are narrowed, and these portions surround the wearer's legs. A nonwoven fabric is suitable for the outer sheet 12, but it is not limited thereto. The type of the nonwoven fabric is not particularly limited. As a raw material fiber, for example, in addition to synthetic fibers such as olefin type such as polyethylene or polypropylene, polyester type, and polyamide type, regenerated fibers such as rayon and cupra, and natural fibers such as cotton can be used. As a processing method, a spun lace method, a spun bond method, a thermal bond method, an air through method, a needle punch method, and the like can be used. However, a long-fiber nonwoven fabric such as a spun-bonded nonwoven fabric, an SMS nonwoven fabric, and an SMMS nonwoven fabric is preferable in that good texture and strength can be compatible. In addition to using a single piece of nonwoven fabric, it is also possible to use multiple nonwoven fabrics in layers. In the latter case, it is preferable that the nonwoven fabrics are adhered to each other with a hot melt adhesive or the like. When a nonwoven fabric is used, the basis weight of the fiber is desirably 10 to 50 g/m$^2$, particularly desirably 15 to 30 g/m$^2$. The outer sheet 12 can be omitted, and in that case, the liquid impervious sheet 11 can have the same shape as that of the outer sheet 12, such that the external surface of a product can be formed.

(Liquid Impervious Sheet)

Although the material of the liquid impervious sheet 11 is not particularly limited, for example, an olefin resin such as polyethylene or polypropylene, a laminated nonwoven fabric obtained by stacking a nonwoven fabric on a polyethylene sheet or the like, a nonwoven fabric in which liquid permeability is substantially secured through a water proof film (in this case, a liquid impervious sheet is formed by the waterproof film and the nonwoven fabric) can be exemplified. Obviously, besides this, in recent years, liquid impervious and moisture permeable materials which have been favorably used from the standpoint of prevention of stuffiness can also be exemplified. As a sheet of this liquid-impervious and moisture-permeable material, for example, a microporous sheet can be exemplified which is obtained by kneading an olefin resin such as polyethylene resin or polypropylene resin and an inorganic filler, forming a sheet with the kneaded materials and monoaxially or biaxially stretching the sheet. Further, nonwoven fabrics using micro denier fibers and a liquid impervious sheet that is not using a water proof film can also be used as the liquid impervious sheet 11. The sheet has liquid impermeability by having high leak proof by reducing air gaps of fibers by heating or applying pressure and by applying a superabsorbent resin, a hydrophobic resin, or a water repellent agent.

(Top Sheet)

As the top sheet 30, a porous or non-porous nonwoven fabric having liquid permeability can be used. The type of constituent fibers of the nonwoven fabric is not particularly limited. Examples of the constituent fibers can include synthetic fibers such as olefin type such as polyethylene and polypropylene, polyester type, and polyamide type, regenerated fibers such as rayon and cupra, natural fibers such as cotton, mixed fibers and conjugate fibers in which two or more of these are used, and the like. Further, the nonwoven fabric may be manufactured by any processing. Examples of processing methods can include known methods such as a spun lace method, a spun bond method, a thermal bond method, a melt blown method, a needle punch method, an air through method, and a point bond method. For example, the spun lace method is preferable when flexibility and drapeability are required, and the thermal bond method is preferable when bulkiness and softness are required.

(Intermediate Sheet)

The intermediate sheet 40 is bonded to the back surface of the top sheet 30 to promptly move excretion liquid passing through the top sheet 30 to the side of the absorber 50 and to prevent returning. For bonding between the intermediate sheet 40 and the top sheet 30, heat embossing or ultrasonic welding can be used in addition to using a hot melt adhesive. As the intermediate sheet 40, a resin film having a large number of through holes can be used in addition to using a nonwoven fabric. As the nonwoven fabric, a material similar to that described in the section of the top sheet 30 can be used. However, the material having a higher hydrophilicity than that of the top sheet 30 or the material having a high fiber density is preferable since those have excellent liquid transfer characteristics from the top sheet 30 to the intermediate sheet 40.

Although the intermediate sheet 40 in the illustrated embodiment is shorter than the width of the absorber 50 and disposed at the center portion, it may be provided over the maximum width. The length of the intermediate sheet 40 in the front-back direction LD may be the same as the entire length of a diaper, may be the same as the length of the absorber 50, or may be within a short length range around a region receiving a liquid.

(Three-Dimensional Side Gather)

To prevent lateral movement of excrement on the top sheet 30 and to prevent lateral leakage, it is preferable to provide the three-dimensional side gathers 60 projecting (standing) from the inner faces on the both sides of a product in the width direction WD.

Figure 3:
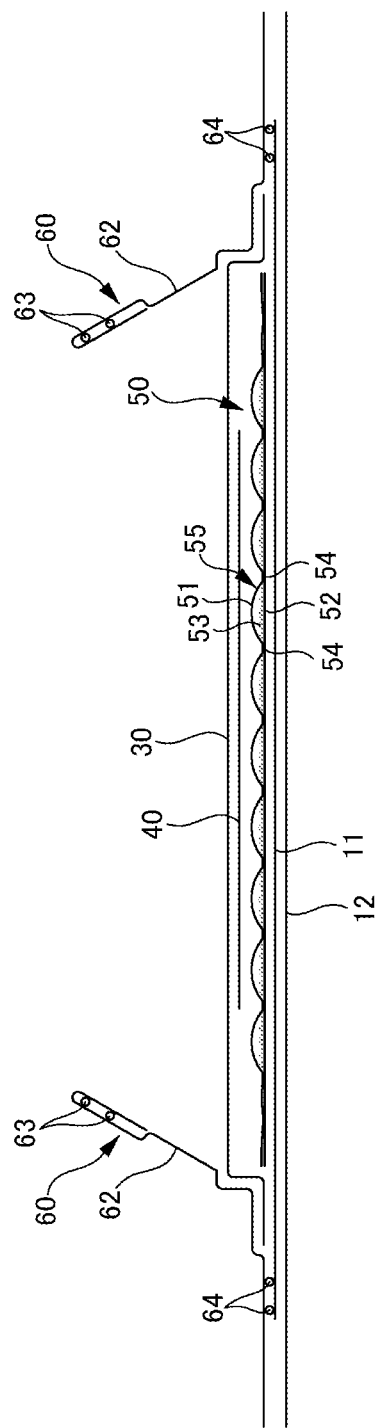
FIG. 3 is a cross-sectional view taken along line 6-6 in FIG. 1.
Figure 4:
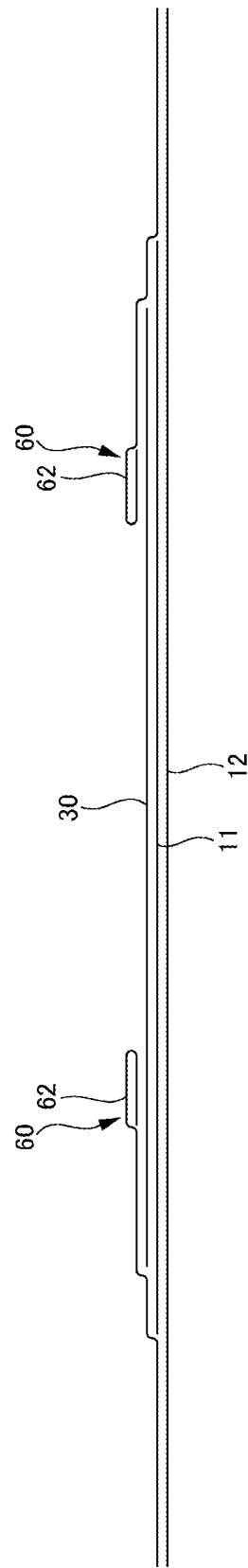
FIG. 4 is a cross-sectional view taken along line 7-7 in FIG. 1.
Figure 5:
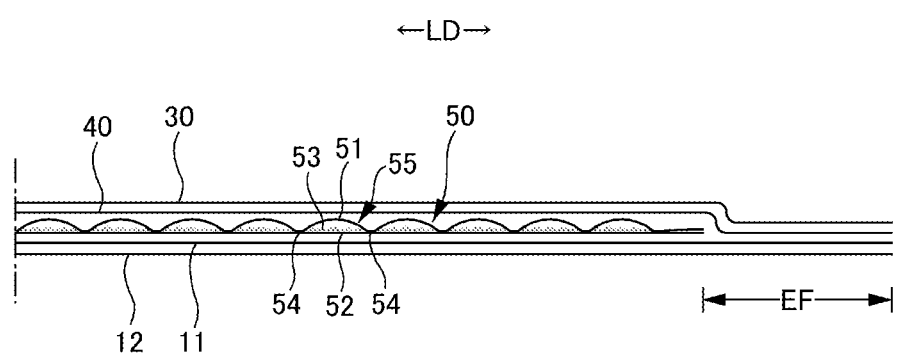
FIG. 5(*a*) is a cross-sectional view taken along line 8-8 in FIG. 1, and FIG. 5(*b*) is a cross-sectional view taken along line 9-9 in FIG. 1.
Figure 5:
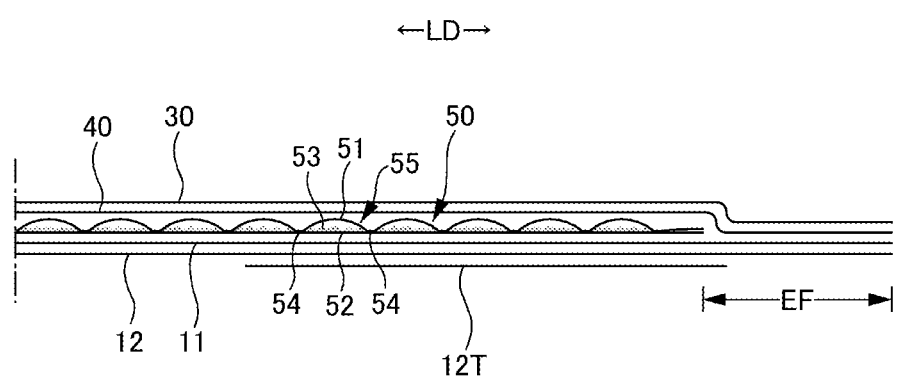

Each three-dimensional side gather 60 is composed of a gather sheet 62 and one or plurality of elongated elastically stretchable members 63 fixed to the gather sheet 62 in a stretched state along the front-back direction LD. As this gather sheet 62, a water repellent nonwoven fabric can be used, and rubber thread or the like can be used as the elastically stretchable member 63. As illustrated in FIGS. 1 and 3, a plurality of the elastically stretchable members may be provided on each side, or only one elastically stretchable members may be provided on each side.

The inner surface of the gather sheet 62 has a fixed start point in the width direction WD on the side portion of the top sheet 30. A portion outside in the width direction WD from this fixed start point is fixed with a hot melt adhesive or the like to the side portion of the liquid impervious sheet 11 and the side portion of the outer sheet 12 positioned at the outside portion.

In the periphery of the leg, the inside in the width direction WD from the fixed start point of each three-dimensional side gather 60 is fixed on the top sheet 30 at both ends of the product in the front-back direction LD. However, the portion therebetween is a non-fixed free portion erected by contraction force of one or plurality of the elastically stretchable members 63. Since a diaper is attached to the body in a boat shape in wearing the diaper, and the contraction force of one or plurality of the elastically stretchable members 63 acts, the three-dimensional side gathers 60 erect by the contraction force of one or plurality of the elastically stretchable members 63 and come in close contact with the legs. As a result, so-called lateral leakage from around the legs is prevented.

Unlike the illustrated embodiment, both end portions in the front-back direction LD in the portion of the inside in the width direction WD of each gather sheet 62 are fixed in a state folded in two having a base end side portion, which extends inward from a portion outside in the width direction WD and a tip side portion, which is folded back on the body side from the end edge on the center side in the width direction WD of the base end side portion and extending outward in the width direction WD, and the portion therebetween may be a non-fixed free portion.

(Flat Gather)

Figure 2:
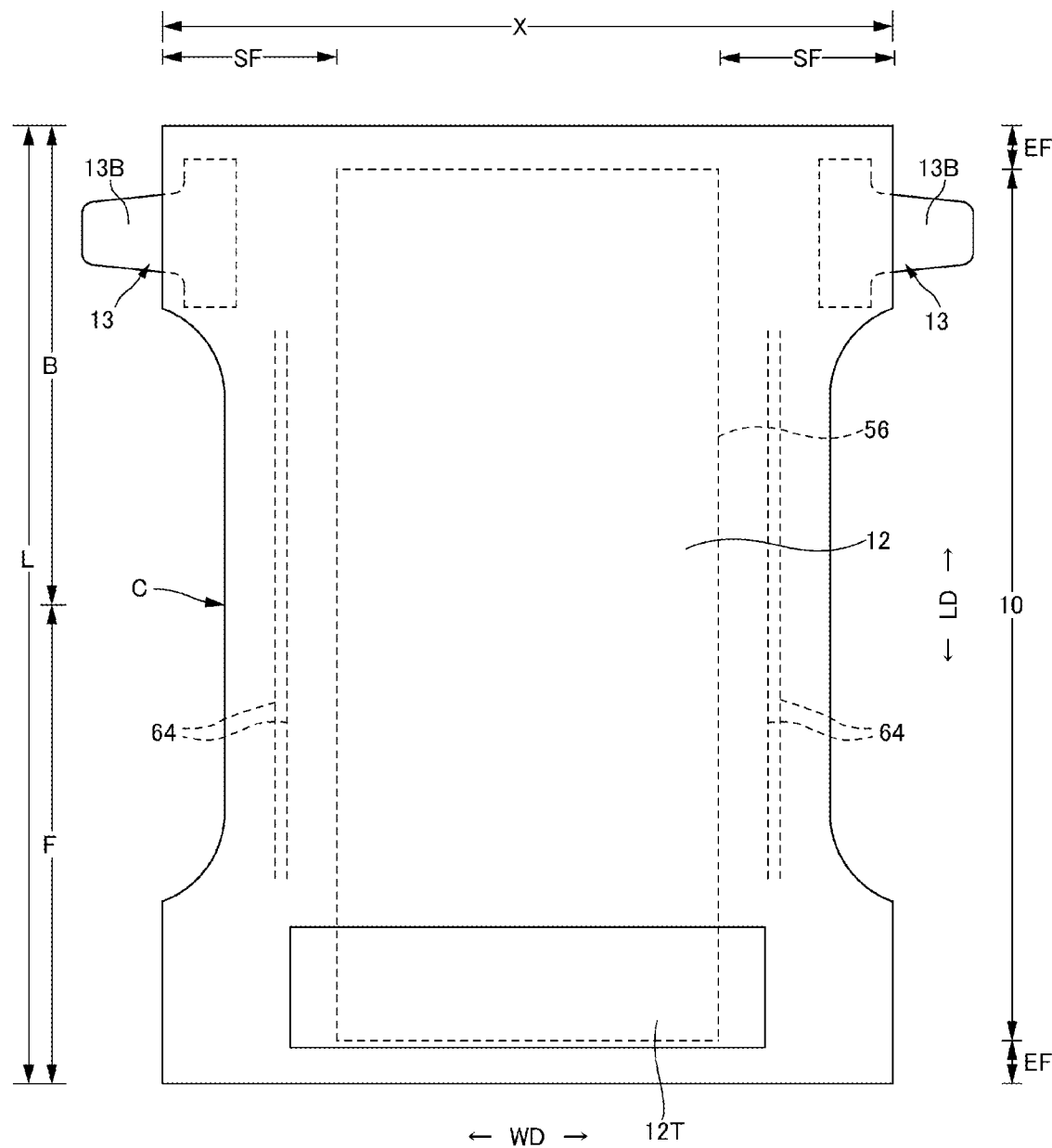
FIG. 2 is a plan view illustrating the external surface of a tape-type disposable diaper in a state where a diaper is spread.

As illustrated in FIGS. 1 to 3, in each side flap portion SF, on the outside in the width direction WD in the vicinity of the fixed start point of the fixed portion of the gather sheet 62, between the gather sheet 62 and the liquid impervious sheet 11, the elastically stretchable members 64, which are made of rubber threads or the like, around the leg portions are fixed in a state stretching along the front-back direction LD, whereby the leg portion of each side flap portion SF is formed as a flat gather. The elastically stretchable members 64 around each leg portion can also be disposed between the liquid impervious sheet 11 and the outer sheet 12 in the side flap portion SF. As in the illustrated example, a plurality of elastically stretchable members 64 around the leg portions may be provided on each side, or only one elastically stretchable member 64 may be provided on each side.

(Fastening Tape)

Figure 6:
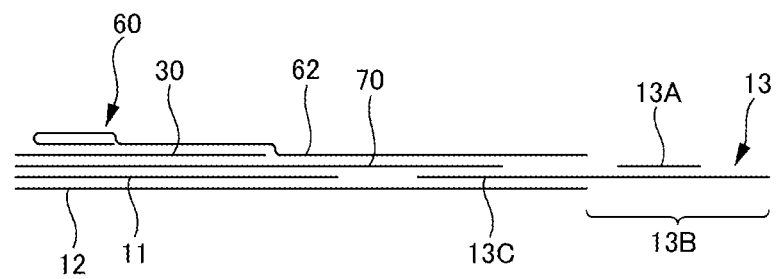
FIG. 6 is a cross-sectional view taken along line 5-5 in FIG. 1.

As illustrated in FIGS. 1, 2, and 6, each fastening tape 13 includes a sheet base material forming a tape attaching portion 13C fixed to the side portion of a diaper and a tape main unit section 13B projecting from the tape attaching portion 13C, and an engagement portion 13A with respect to the ventral side, which is provided in the middle portion in the width direction WD of the tape main unit section 13B in the seat base material. A tip end side from the engagement portion 13A is a tab part. The tape attaching portion 13C of the fastening tape 13 is sandwiched between the gather sheet 62 forming an inner layer in the side flap portion and the outer sheet 12 forming an outer layer. The tape attaching portion 13C is adhered to the both sheets 62 and 12 with a hot melt adhesive. In addition, the engagement portion 13A is bonded to the sheet base material with an adhesive so that it cannot be removed.

A hook member (male member) of a mechanical fastener (hook and loop fastener) is suitable as the engagement portion 13A. The hook member has a large number of engagement projections on its external surface side. The engagement projection has a check mark shape, a J shape, a mushroom shape, a T shape, and a double J shape (a shape bonded back to back of a J shape), but may have any shape. Obviously, an adhesive material layer can also be provided as an engagement portion of the fastening tape 13.

As the sheet base material forming from the tape attaching portion to the tape main unit section, in addition to various nonwoven fabrics such as a spunbonded nonwoven fabric, an air-through nonwoven fabric, and a spunlace nonwoven fabric, a plastic film, a polyethylene laminated nonwoven fabric, paper, or a composite material thereof can be used.

(Target Sheet)

It is preferable to provide a target sheet 12T having a target for facilitating engagement at the engagement portion of each fastening tape 13 in the ventral side portion F. In the case where the engagement portion is the hook member 13A, the target sheet 12T can be used having a large number of loops made of threads to which engagement projections of the hook member are tangled, are provided on a surface of the sheet base member made of a plastic film or a nonwoven fabric. Further, in the case of an adhesive layer, it is possible to use a sheet base material made of a plastic film having a smooth surface with high adhesiveness and subjected to a release treatment. In the case where the engagement portion of the fastening tape 13 in the ventral side portion F is made of a nonwoven fabric, for example, when the outer sheet 12 in the illustrated embodiment is made of a nonwoven fabric, and the engagement portion of the fastening tape 13 is the hook member 13A, the target sheet 12T may be omitted, and the hook member 13A can be entangled and engaged with the nonwoven fabric of the outer sheet 12. In this case, the target sheet 12T may be provided between the outer sheet 12 and the liquid impervious sheet 11.

(Absorber)

The absorber 50 is a part that absorbs and retains liquid content of excrement. The absorber 50 can be adhered to the components on at least one of the front surface side and back surfaces side via an adhesive such as a hot melt adhesive.

Figure 7:
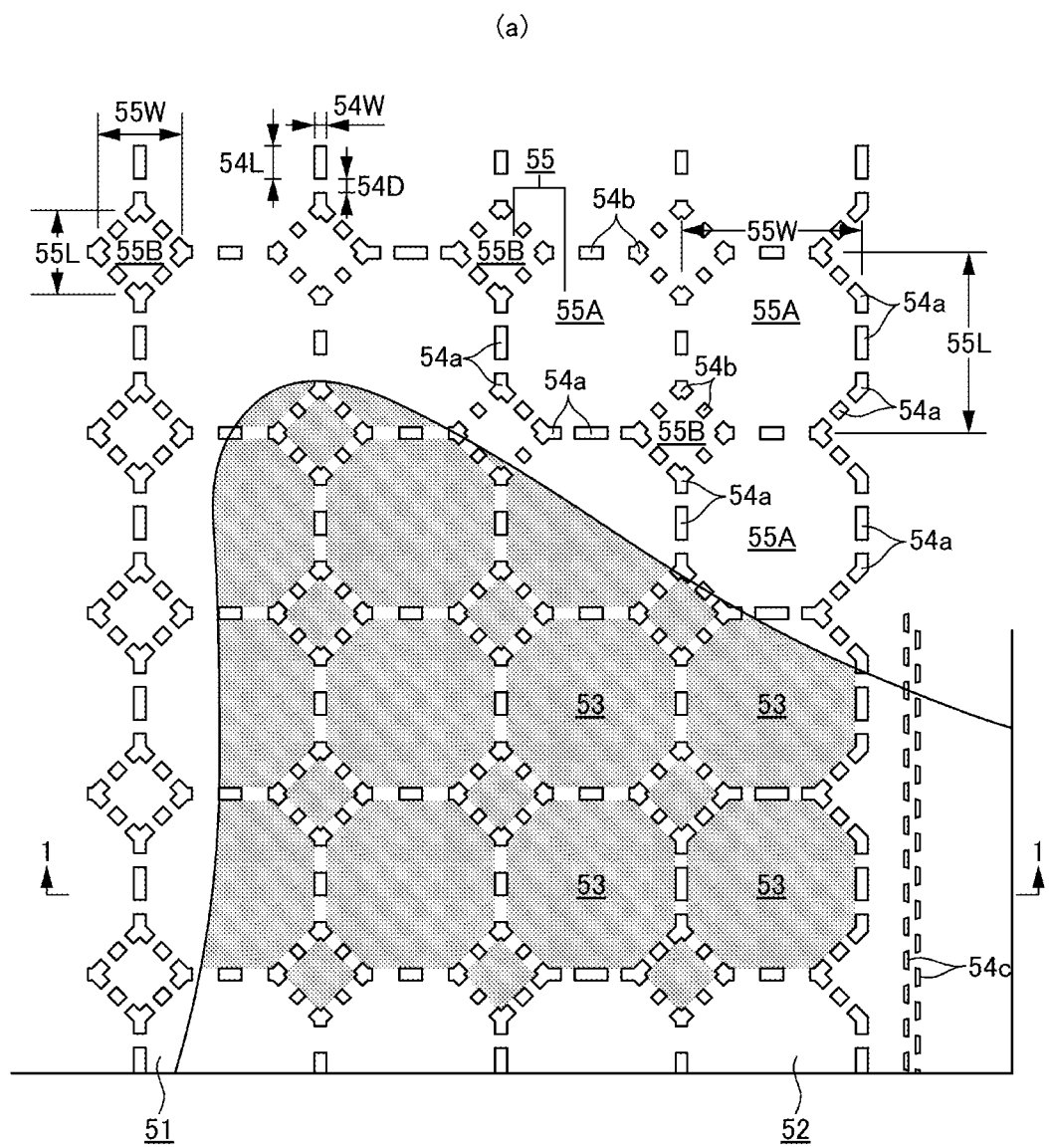
FIG. 7(*a*) is a fragmentary plan view of a main part of an absorber, and FIG. 7(*b*) is a cross-sectional view taken along line 1-1 of FIG. 7(*a*).
Figure 7:
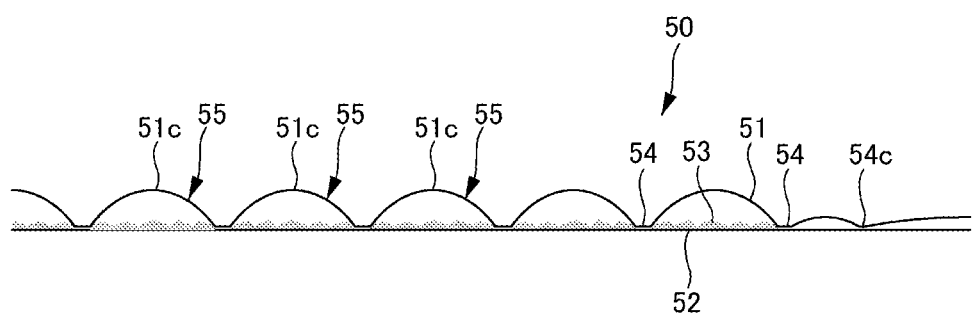

As illustrated in the enlarged view of FIG. 7, the absorber 50 is a cell absorber 50 having the front surface side sheet 51; the back surface side sheet 52 disposed on the back surface side of the front surface side sheet 51; the cells (small chambers) 55 each of which is surrounded by the bonded portions 54 of the front surface side sheet 51 and the back surface side sheet 52, and in each of which the front surface side sheet 51 and the back surface side sheet 52 are not bonded; and the superabsorbent polymer particles 53 contained in each of the cells 55. In this way, by distributing and retaining the superabsorbent polymer particles 53 in a large number of the cells 55 each of which is surrounded by the bonded portion 54, the uneven distribution of the superabsorbent polymer particles 53 in the absorber 50 can be prevented. The cell absorber 50 can be wrapped with a wrapping sheet (not illustrated). In this case, one wrapping sheet can be wrapped in a cylindrical shape so as to surround the absorber on the front and back surfaces and the both side surfaces of the absorber 50 and two wrapping sheets can be also wrapped so as to sandwich the absorber from both the front surface side and the back surface side. As the wrapping sheet, tissue paper, particularly crepe paper, a nonwoven fabric, a polyethylene laminated nonwoven fabric, a sheet with small holes, and the like can be used. However, it is desirable that the wrapping sheet be a sheet through which the superabsorbent polymer particles do not pass. When a nonwoven fabric is used for the wrapping sheet, a hydrophilic SMS nonwoven fabric (SMS, SSMMS, etc.) is particularly suitable, and polypropylene and polyethylene/polypropylene composite material can be used as a material. The basis weight is preferably 5 to 40 $g/m^2$, particularly preferably 10 to 30 $g/m^2$. When the cell absorber 50 is wrapped with the wrapping sheet(s), pulp fibers can be accumulated on one side of the front surface side and the back surface side of the cell absorber, and the cell absorber together with the pulp fibers can be wrapped with the wrapping sheet(s) collectively.

The front surface side sheet 51 may be a liquid-pervious material or a liquid impervious material, but preferably it is a liquid-pervious material when it is positioned on the top sheet 30 side as indicated in the illustrated embodiment. Similarly to the top sheet 30, a porous or non-porous nonwoven fabric or a porous plastic sheet can be used for the front surface side sheet 51. In the case of using a nonwoven fabric for the front surface side sheet 51, examples of the constituent fibers include synthetic fibers (including not only single component fibers but also conjugate fibers) such as olefin type such as polyethylene or polypropylene, polyester type, and polyamide type, regenerated fibers such as rayon and cupra, and natural fibers such as cotton, but it can be selected without limitation, and it is preferable to use a thermoplastic resin fiber because of excellent thermal processability. The fiber bonding method of the nonwoven fabric is not particularly limited, but to prevent the superabsorbent polymer particles 53 from falling off through the sheet, it is preferable to use a bonding method which increases fiber density, such as a spun bond method, a meltblown method, and a needle punch method. In the case of using a porous plastic sheet, its pore diameter is preferably smaller than the outer shape of the superabsorbent polymer particle 53 to prevent the superabsorbent polymer particle 53 from falling off through the sheet. When the material of the front surface side sheet 51 is hydrophobic, a hydrophilic agent can also be contained.

To facilitate the arrangement of the superabsorbent polymer particles 53 in manufacturing and to secure the volume after the swelling upon the absorption, in the portion forming each cell 55 in the front surface side sheet 51, recesses 51c recessed from the back surface side to the front surface side are preferably formed, but it may not be formed.

The back surface side sheet 52 may be made of the same material as the front surface side sheet 51, but in the case where the front surface side sheet 51 is composed of a liquid pervious material, a liquid impervious material can be used for the back surface side sheet 52. The liquid impervious material usable for the back surface side sheet 52 can be appropriately selected and used from the materials described in the section of the liquid impervious sheet 11. Although not illustrated, the front surface side sheet 51 and the back surface side sheet 52 may be one side layer and another side layer in which one sheet of material is folded in two.

The superabsorbent polymer particles 53 may not be fixed to the front surface side sheet 51 and the back surface side sheet 52, may be freely movable, and also can be bonded or adhered to the front surface side sheet 51 and the back surface side sheet 52. Further, the superabsorbent polymer particles 53 may be agglomerated to some extent.

As the superabsorbent polymer particles 53, those used for this type of absorbent articles can be used on an as-is basis. The particle diameter of the superabsorbent polymer particles is not particularly limited, but for example, when the particles are sieved (shaking for five minutes) using a standard sieve (JIS Z8801-1:2006) of 500 μm and the particles subjected to sieving with the 500 μm standard sieve are further sieved (shaking for five minutes) using the standard sieve (JIS Z8801-1: 2006) of 180 μm, preferably the proportion of the particles remaining on the 500 μm standard sieve is 30% by weight or less, and the proportion of the particles remaining on the 180 μm standard sieve is 60% by weight or more.

The material of the superabsorbent polymer particles 53 can be used without particular limitation, but the material having the water absorption capacity of 40 g/g or more is suitable. Examples of the superabsorbent polymer particles 53 include starch-based, cellulose-based, and synthetic polymer-based, and starch-acrylic acid (salt) graft copolymers, saponified starch-acrylonitrile copolymers, sodium carboxymethyl cellulose crosslinked products, acrylic acid (salt) polymers, and the like. As the shape of the superabsorbent polymer particles 53, the shapes of particulate materials which are usually used are suitable, but other shapes can also be used.

The superabsorbent polymer particles 53 having a water absorption rate of 70 seconds or less, particularly 40 seconds or less, are suitably used. If the water absorption rate is too slow, back-flow, in which the liquid fed into the absorber 50 returns to the outside of the absorber 50, is likely to occur.

The superabsorbent polymer particles 53 having the gel strength of 1,000 Pa or more are preferably used. Thereby, even when the absorber 50 is bulky, it is possible to effectively suppress stickiness after liquid absorption.

The basis weight of the superabsorbent polymer particles 53 can be appropriately determined according to the absorption amount required for the use of the absorber 50. Therefore, although it cannot be said unconditionally, the basis weight can be 50 to 350 g/m². When the basis weight of the polymer is less than 50 g/m², it is difficult to secure the absorption amount. When it exceeds 350 g/m², the effect is saturated.

It is desirable that the bonded portion 54 for bonding the front surface side sheet 51 and the back surface side sheet 52 be bonded by welding the front surface side sheet 51 and the back surface side sheet 52 like ultrasonic welding or heat sealing, but it may be bonded with a hot melt adhesive.

The bonded portions 54 of the front surface side sheet 51 and the back surface side sheet 52 are arranged in dotted line shapes along the following pattern. In the pattern, the same-sized octagonal portions and diamond shaped portions each having four equal sides are arranged without any space in the front-back direction and the width direction. In each octagonal portion, all eight interior angles are 135°, and the lengths of the two pairs of opposite sides whose facing directions are mutually orthogonal are equal. As a result of this, the absorber includes octagonal cells 55A surrounded by the octagonal portions of the bonded portions 54 and diamond-shaped cells 55B surrounded by the diamond-shaped portions of the bonded portions 54 are included.

Examples of the same-sized octagons each having all eight interior angles of 135°, and having two pairs of opposite sides whose facing directions are mutually orthogonal are equal in length, include, in addition to a regular octagon in which all sides are equal in length; an octagon in which the length of the oblique side (common side with a diamond-shaped portion) is shorter than the length of the side along the front-back direction LD and the width direction WD, and due to which an adjacent diamond-shaped portion is small; and an octagon in which, on the contrary, the length of the oblique side is longer than the length of the side along the front-back direction LD and the width direction WD, and due to which the adjacent diamond-shaped portion is large. Considering the absorption capacity at the initial stage of absorption, it is preferable that the octagon has a shape due to which the adjacent diamond shape is small, and the length of the oblique side is the same as or smaller than the length of the side along the front-back direction LD and the width direction WD, and it is particularly preferable that the lengths are the same (regular octagon). The size of each cell 55 can be appropriately determined, and for example, each of the length 55L in the front-back direction LD and the length 55W in the width direction WD of the octagonal cell 55A can be about 10 to 25 mm, and each of the length 55L in the front-back direction and the length 55W of the width direction WD of the diamond-shaped cell 55B can be about 6 to 15 mm The bonded portions 54 may be formed in a continuous liner shape. In the case where the bonded portions 54 are formed in a dotted line shape (intermittently), it is desirable that the superabsorbent polymer particles 53 be not present in the bonded portions 54, but the superabsorbent polymer particles may be incorporated therein. In the case where the bonded portions 54 are formed in a dotted line shape (intermittently), the superabsorbent polymer particles 53 are not present between the bonded portions 54 (point interval portion) in the direction surrounding each of the cells 55 or are supposed to be less than those in the cell 55, even if they are present therein.

When the superabsorbent polymer particles 53 in each cell 55 are swollen upon the absorption to fill the inside of the cell 55, if the front surface side sheet 51 and the back surface side sheet 52 are strongly bonded at the bonded portions 54 such that the bonded portions 54 are not peeled off due to the internal pressure, there is a possibility that the absorption amount and absorption rate are lowered due to inhibition by the swelling and so-called gel blocking when the superabsorbent polymer particles 53 fill in the cell 55. Therefore, the bonded portions 54 positioned at least on continuous two sides of each octagonal cell 55A are formed as weak bonded portions 54b which can be peeled off by the swelling force of the superabsorbent polymer particles 53 in the cell 55 adjacent to these bonded portions 54, and it is preferable that the cells 55 adjacent to these bonded portions 54 are coalesced by peeling off of the weak bonded portions 54b to form a large cell 55. Such a function can be realized by providing weak bonded portions with decreased bonding strength at appropriate positions and by determining the type and amount of the superabsorbent polymer particles 53 disposed in each cell 55 such that the volume of the superabsorbent polymer particles 53 in the cell 55 upon the saturation absorption, becomes sufficiently larger than the volume of the cell 55.

In the combination pattern of octagons and diamond shapes, each side of the diamond shape is common to the side in the oblique direction of the octagon, and the octagons, which are adjacent to each other in the front-back direction LD and the octagons, which are adjacent to each other in the width direction WD have the adjacent sides in common, such that, due to the swelling pressure in the octagonal cell 55A, the peeling force is applied to both the bonded portions 54 which are common and the bonded portions which are non-common to those of the side of the adjacent diamond shape. Comparing with other shapes with the same area, the octagonal cells 55A, each having all eight interior angles of 135°, and having two pairs of opposite sides whose facing directions are mutually orthogonal are equal in length, have relatively short circumferential lengths. Therefore, in the case where bonded portions 54 surrounding the cell 55 can be peeled off due to the swelling of the superabsorbent polymer particles 53 in the cell 55A, the bonded portions 54 can be peeled off with the weak swelling force. Therefore, when the bonded portions 54 and the cells 55 are provided according to the combination pattern of the octagons and diamond shapes, the adjacent cells 55 are coalesced more smoothly and rapidly upon the absorption. In addition, if the bonded portions 54 positioned at least on continuous two sides in each octagonal cell 55A are the weak bonded portions 54b, the increase in the volume of the cell 55 relative to the number of coalescence of the coalesced cells 55 is also excellent. Therefore, it is possible to efficiently increase the volume due to the coalescence of the cells 55. (When the octagon is a regular octagon, it is particularly preferable, since the diamond-shaped portion is relatively small, and the circumferential length of the octagon is comparatively short, such that the absorption capacity in the initial stage of the absorption and the ease of peeling off in progressing absorption are well-balanced. In addition, a regular octagon may be elastically deformed from an original regular octagon, which is caused by the stretching and contracting of the first surface sheet 51 and the back surface sheet 52 in manufacturing. Now the term "regular octagon" also includes such a deformed octagon as long as the rate of the deformation within ±5% in the front-back direction LD)

Particularly, since the diamond-shaped cell 55B has a relatively smaller volume than the octagonal cell 55A, in the case where the contained amount of the superabsorbent polymer particles 53 per unit area is the same, when the superabsorbent polymer particles 53 are swollen upon the absorption, the diamond-shaped cells 55B are filled first, and the bonded portions 54 in the oblique direction in the bonded portions 54 surrounding the octagonal cells 55A are first peeled off, and the direct coalescence of the octagonal cells 55A is delayed. Therefore, to enhance the increase in the volume of the cell relative to the number of coalesced cells, it is desirable that the diamond-shaped cells 55B do not contain the superabsorbent polymer particles 53 or contains a smaller amount of the superabsorbent polymer particles 53 per unit area than the octagonal cells 55A (for example, ½ or less, particularly 1/10 or less in terms of the ratio of the basis weight).

Figure 11:
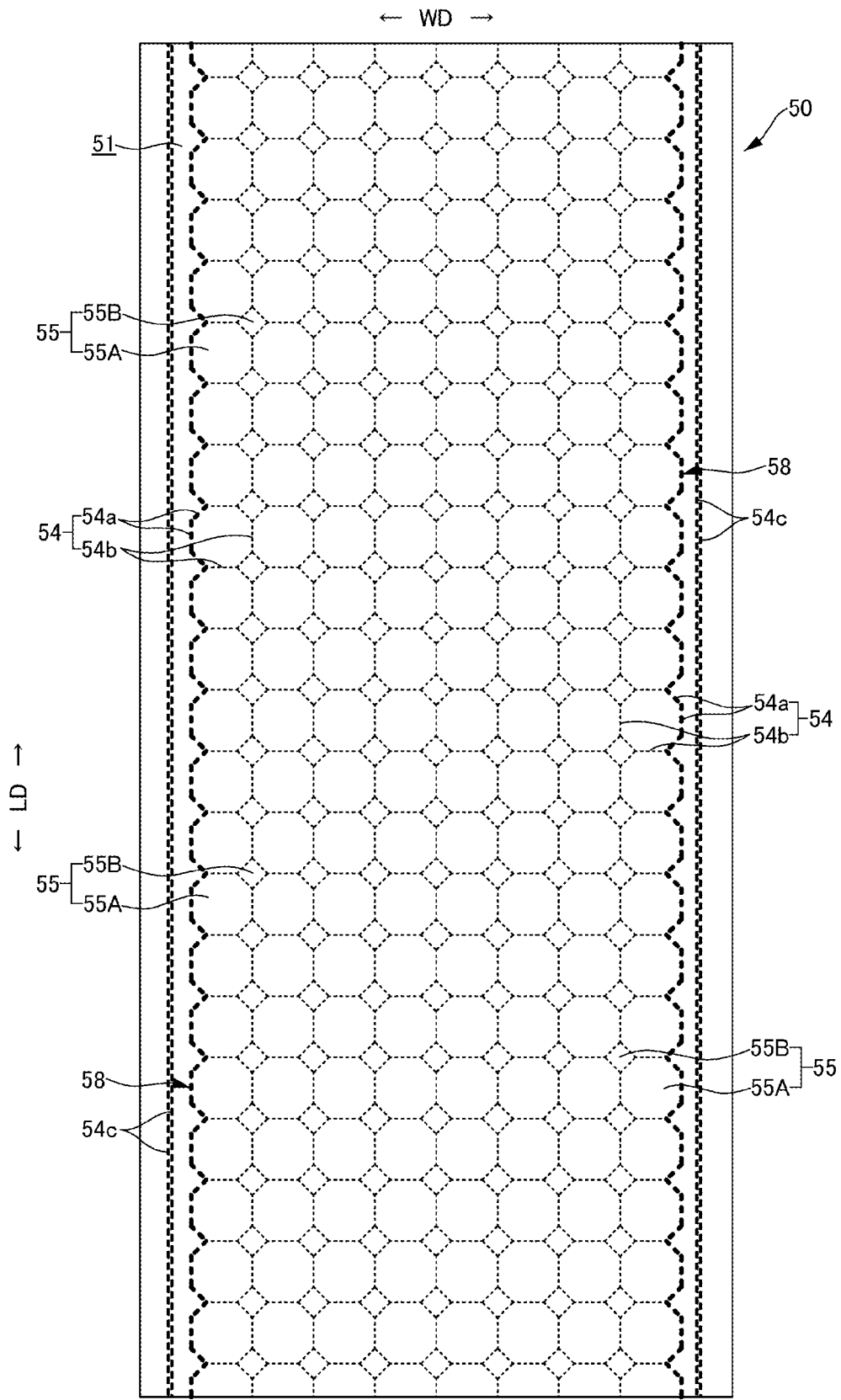
FIG. 11 is a plan view of an absorber illustrating bonded portions in a simplified manner.
Figure 12:
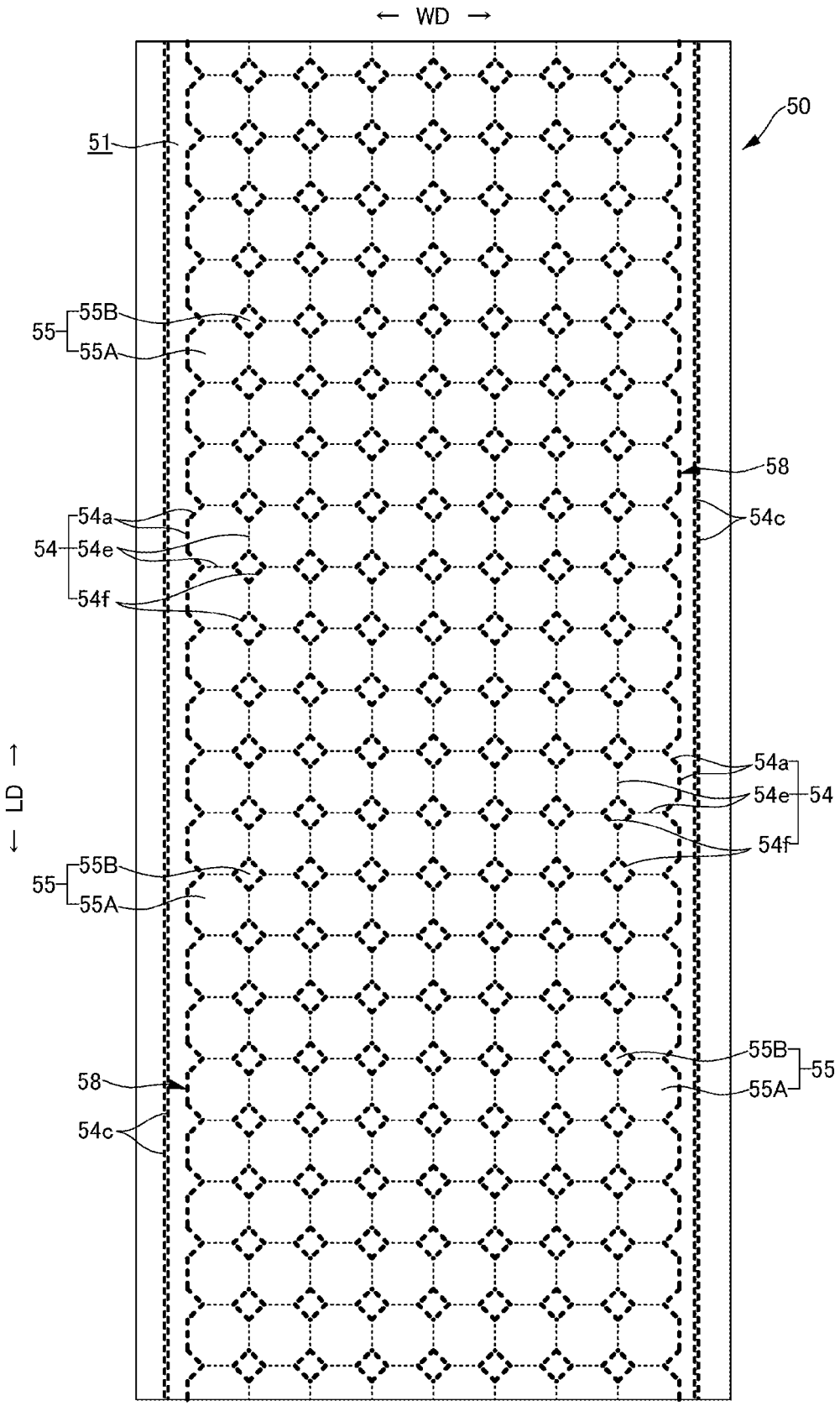
FIG. 12 is a plan view of an absorber illustrating bonded portions in a simplified manner.

As illustrated in FIG. 11 and the like, all of the weak bonded portions 54b can have uniform bonding strength or two-stage bonding strength. For example, one preferred embodiment is that, as illustrated in FIG. 12, in the bonded portions 54 provided in the pattern including the octagonal portions, the first bonded portions 54e positioned on the sides along the front-back direction LD and the width direction WD have lower bonding strength than the second bonded portions 54f positioned on the sides along the oblique direction, and the first bonded portions 54e are peeled off more preferentially than the second bonded portions 54f by the swelling force of the superabsorbent polymer particles. When the first bonded portions 54e and the second bonded portions 54f are peeled off with such a priority order, the first bonded portion 54e are peeled off at the initial stage, and the octagonal cells 55A are coalesced vertically and horizontally to form a large coalesced cell immediately. In addition, since the diamond-shaped cells 55B are depressed low until the second bonded portions 54f are peeled off, the contact area with the skin can be reduced.

Figure 13:
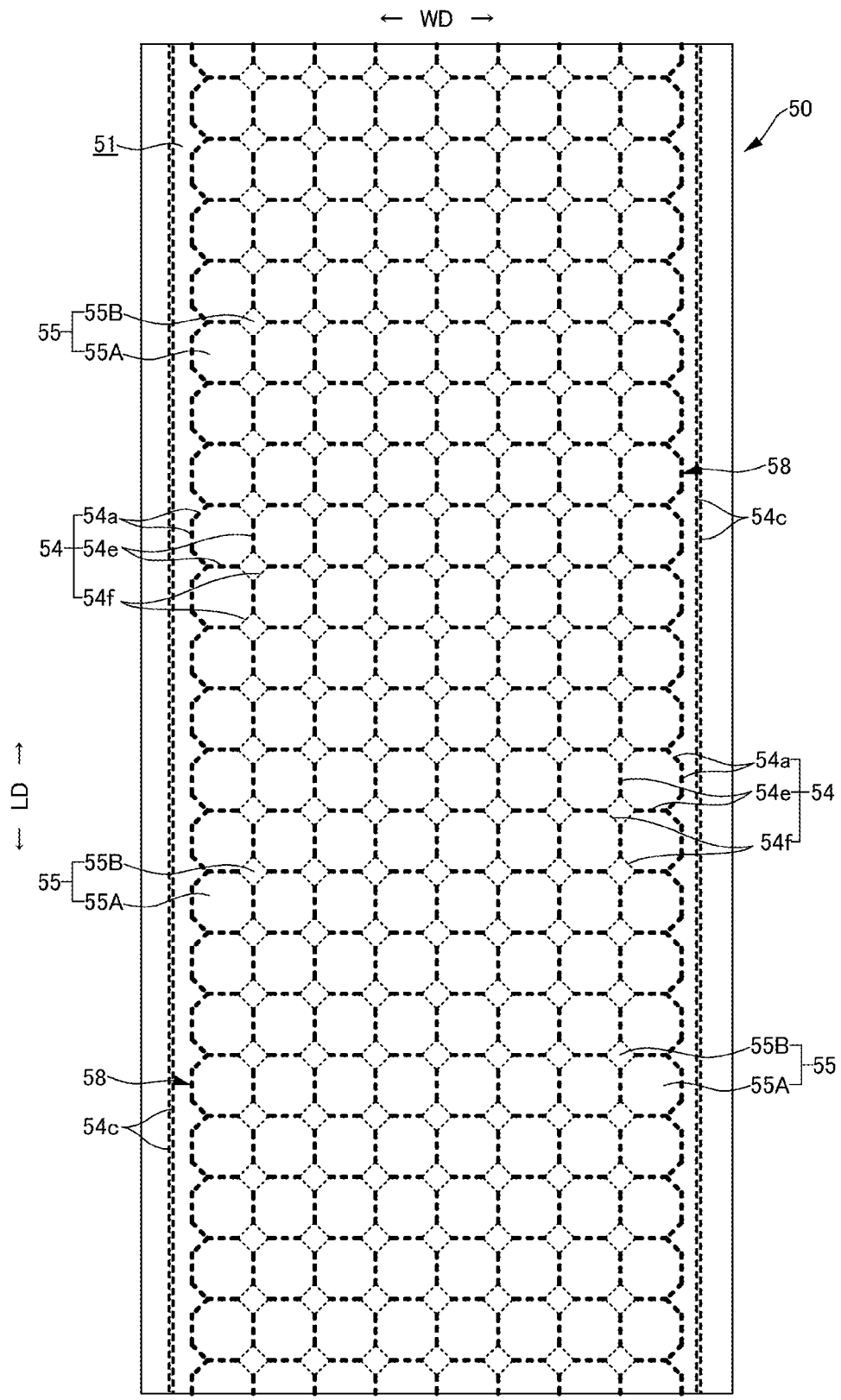
FIG. 13 is a plan view of an absorber illustrating bonded portions in a simplified manner.
Figure 14:
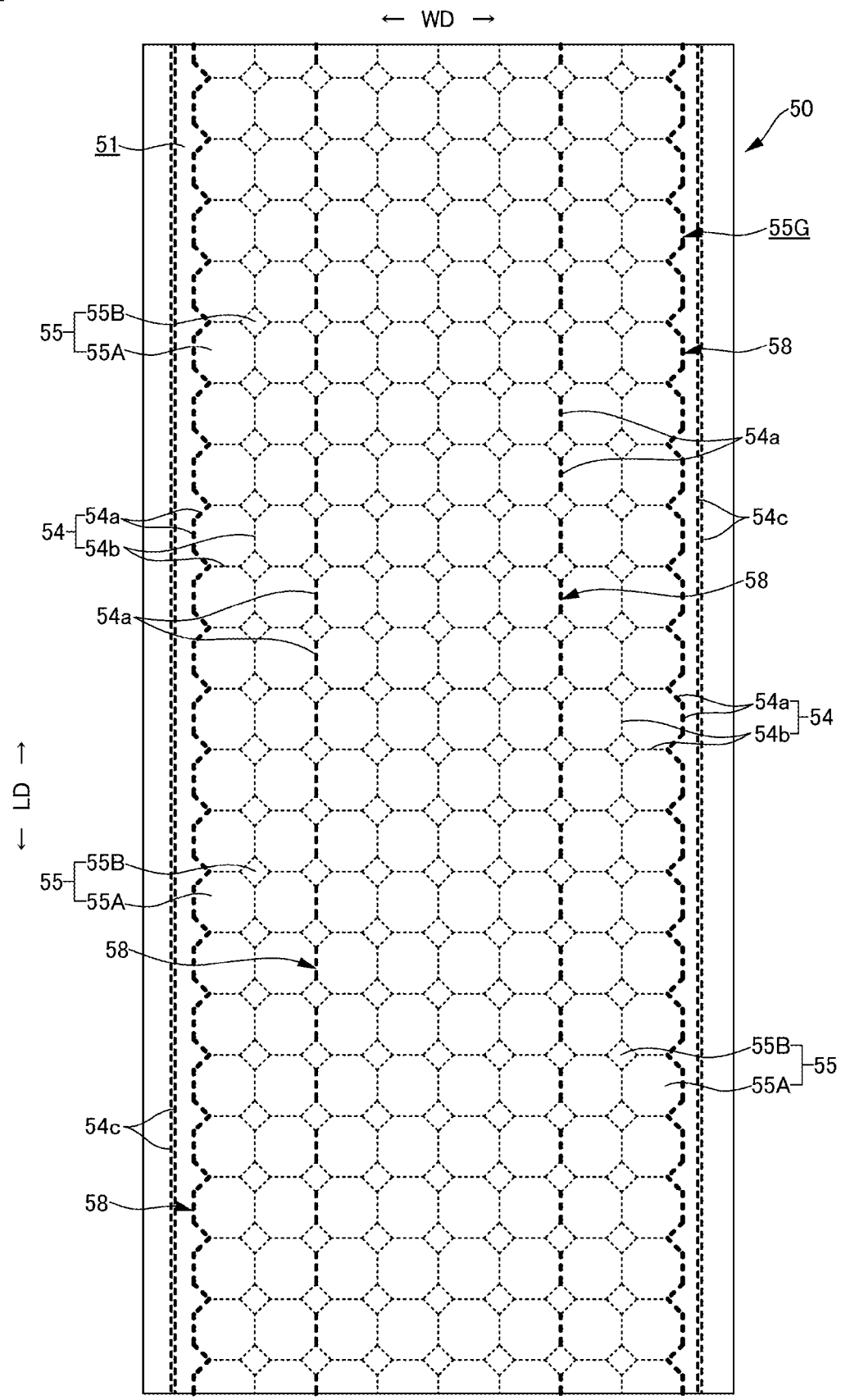
FIG. 14 is a plan view of an absorber illustrating bonded portions in a simplified manner.

Further, the other preferred embodiment is that, as illustrated in FIG. 13, in the bonded portions 54 provided in the pattern including the octagonal portions, the first bonded portions 54e positioned on the sides along the front-back direction LD and the width direction WD have higher bonding strength than the second bonded portions 54f positioned on the sides along the oblique direction, and the second bonded portions 54f are peeled more preferentially than the first bonded portions 54e by the swelling force of the superabsorbent polymer particles. When the bonded portions 54 are peeled off with such a priority order, the second bonded portions 54f are peeled off at the initial stage, and octagonal cells 55A are coalesced in the oblique direction to form a large coalesced cell immediately. In addition, since the first bonded portions 54e can suppress an increase in the thickness of the absorber 50 until the first bonded portions 54e are peeled off, it is possible to prevent a local increase in the thickness of a part of the absorber 50 where liquid is absorbed.

Figure 8:
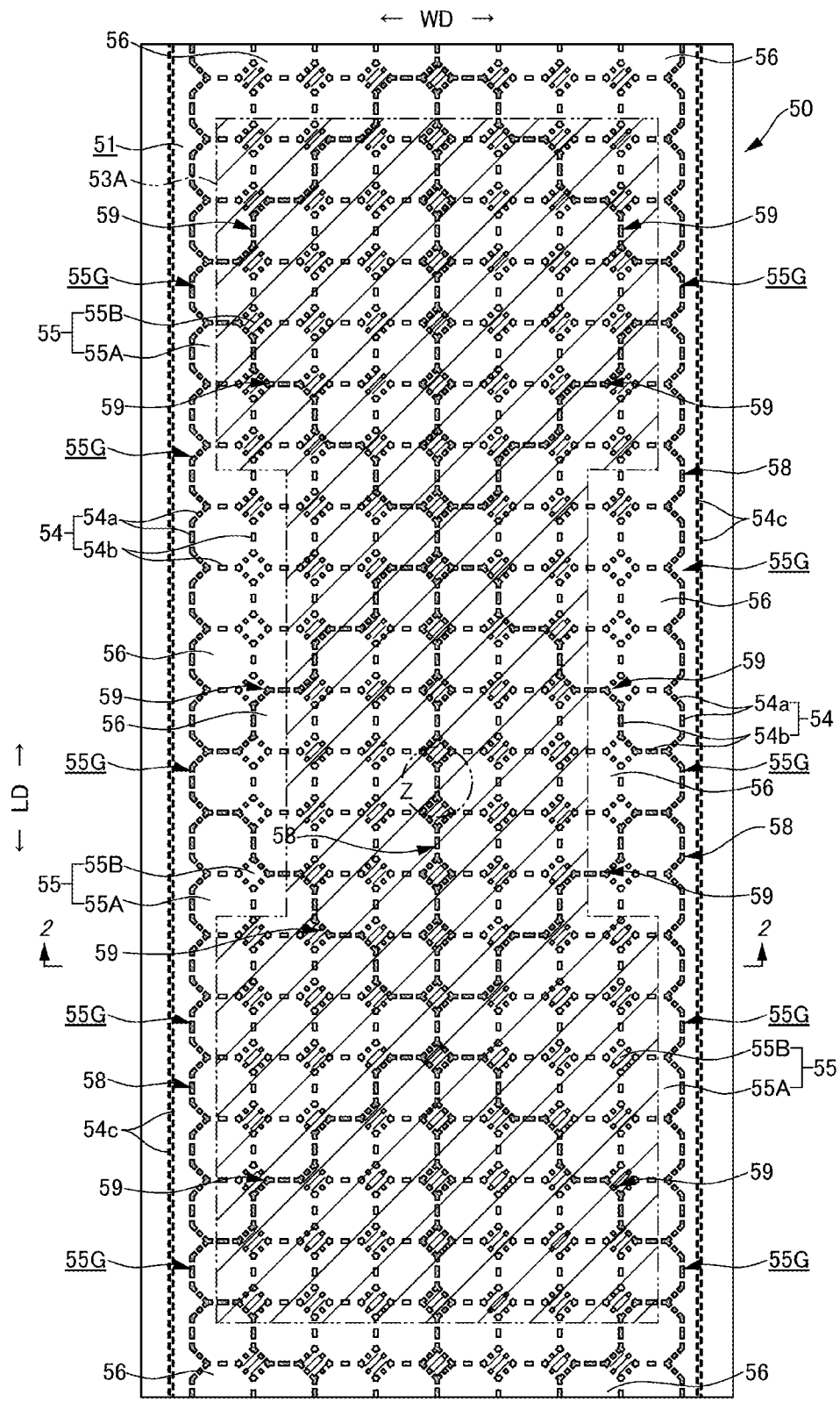
FIG. 8 is a plan view of an absorber.
Figure 9:
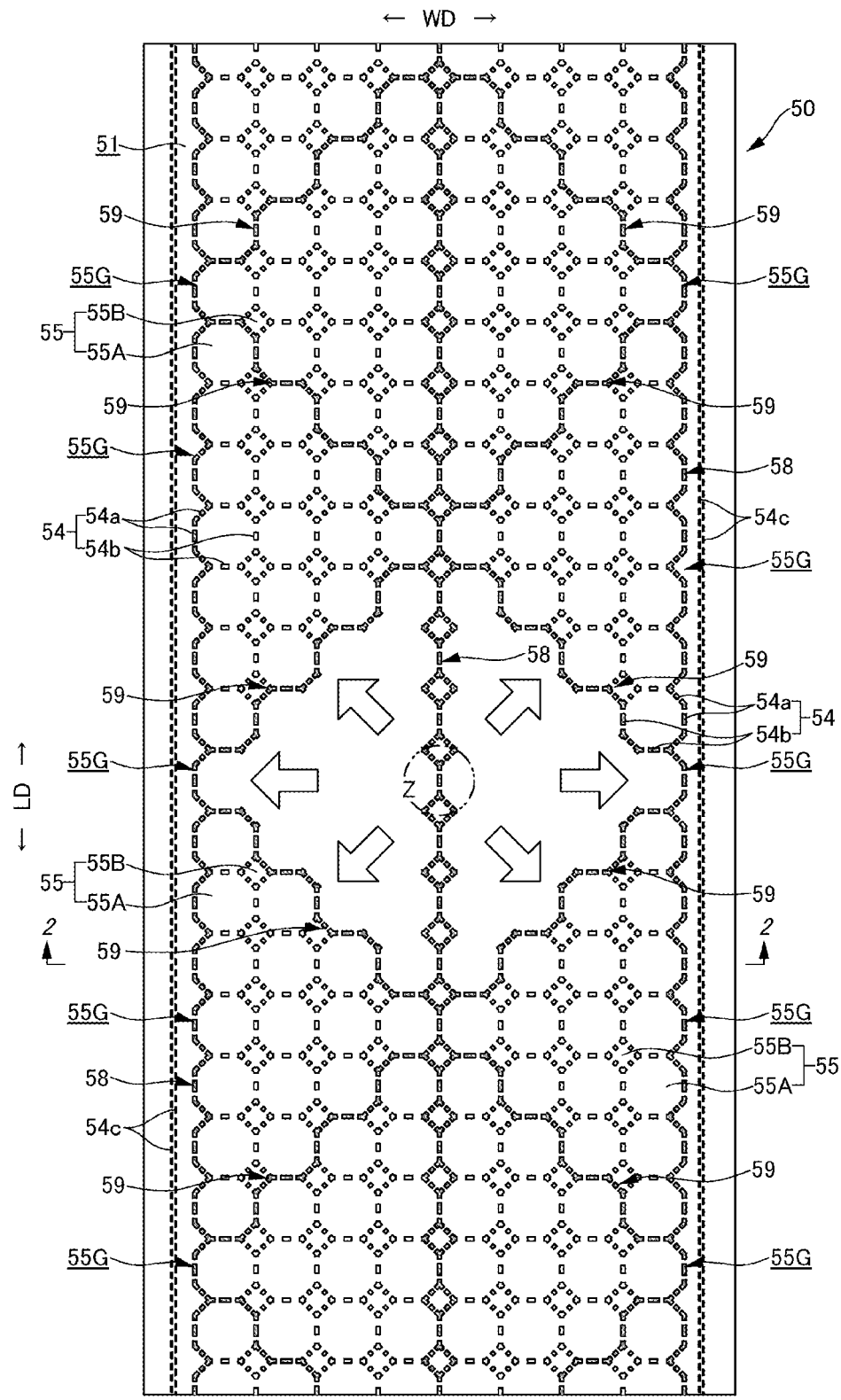
FIG. 9 is a plan view of an absorber.
Figure 10:
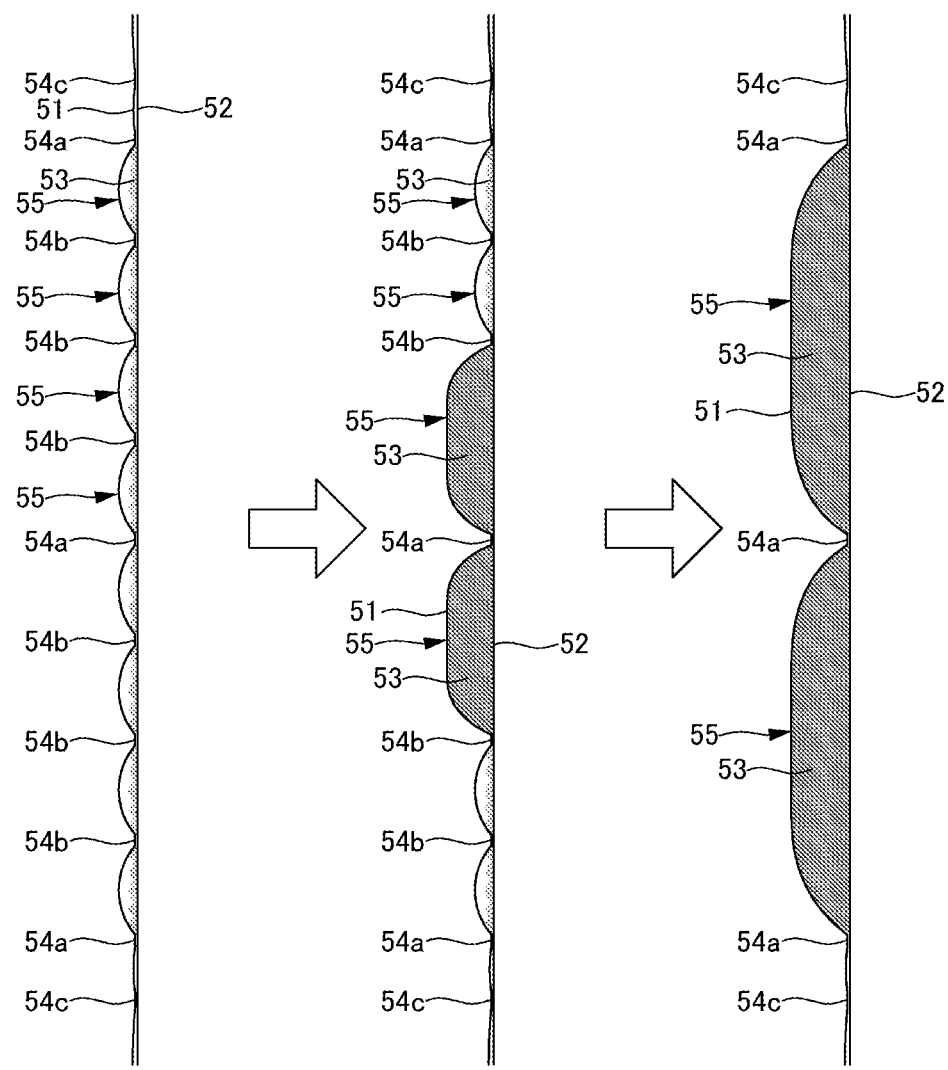
FIG. 10 is cross-sectional views taken along line 2-2 in FIGS. 8 and 9.

All of the bonded portions 54 in the absorber 50 (excluding those located on the outermost side in the width direction) may be weak bonded portions. However, one preferred embodiment is that, as in the embodiments illustrated in FIG. 8 (also refer to FIG. 9), FIGS. 15 and 16, a planar region of the absorber 50 is divided into the maximum enlargement section 55G surrounding a plurality of the cells 55 by the strong bonded portions 54a which are not peeled off due to the swelling force of the superabsorbent polymer particles 53 in the adjacent cells 55, and the bonded portions 54 positioned inside each of the maximum enlargement sections 55G is the weak bonded portions 54b. In this case, all of the weak bonded portions 54b in the maximum enlargement section 55G are peeled off due to the swelling pressure upon the absorption of the superabsorbent polymer particles 53 in the cells 55, so that a single cell 55 is formed throughout in the entire maximum enlargement section 55G. After that, the strong bonded portions 54a surrounding the maximum enlargement section 55G are not peeled off due to the swelling pressure upon the absorption of the superabsorbent polymer particles 53 in the maximum enlargement section 55G, such that the gelled superabsorbent polymer particles 53 swollen upon absorption are hardly to move and collect to a low place such as a crotch portion, comfort in wearing may not be hence deteriorated. For example, in the embodiment illustrated in FIG. 8, assuming that urine is excreted at the position of the symbol Z, the urine is diffused to the periphery around the position as indicated in FIG. 9, and the urine is absorbed in the superabsorbent polymer particles 53 at each position. At this time, as illustrated in FIGS. 9 and 10, as for each cell 55, in which the swelling pressure of the superabsorbent polymer particles 53 inside is increased, the weak bonded portions 54b surrounding the cell 55 cannot resist against the swelling pressure, and the cell 55 is coalesced with the adjacent cells 55. This coalescence continues as long as the weak bonded portions 54b can be peeled off due to the swelling upon the absorption of the superabsorbent polymer particles 53 and proceeds to reach the cells 55 having the strong bonded portions 54a positioned in the sides. Such a function is realized, for example, by determining the type and amount of the superabsorbent polymer particles 53 disposed in each cell 55 such that the volume of the superabsorbent polymer particles 53 in each cell 55 upon the saturation absorption, becomes sufficiently larger than the volume of the cell 55, and the volume of the superabsorbent polymer particles 53 in the maximum enlargement section 55G upon the saturation absorption becomes less than the volume of the coalesced cells in the entire maximum enlargement section 55G surrounded by the strong bonded portions 54a.

The difference in bonding strength may be easily formed by changing the area of each of the bonded portions 54 but is not limited thereto. For example, in the case of forming the bonded portions 54 with a hot melt adhesive, a method in which the type of the hot melt adhesive is varied depending on the positions of the cells can be adopted. In the case of forming the bonded portions 54 by welding the front surface side sheet 51 and the back surface side sheet 52, the weak bonded portions 54b can be formed only by forming the bonded portions 54 into the dotted line shapes and widening the point intervals 54D. However, since the bonded portions 54 can be formed at the boundary between the adjacent cells 55, if the point interval 54D becomes too large, the gaps are increased at the boundary between the adjacent cells 55, which causes the superabsorbent polymer particles 53 to move easily. Therefore, when the weak bonded portions 54b are formed into the dotted line shape by combining and arranging the width of the line width 54W of the bonded portions and the width of the point interval 54D, the weak bonded portions 54b are likely to be peeled off in spite of the narrow gaps.

The size of the bonded portion 54 for bonding the front surface side sheet 51 and the back surface side sheet 52 can be appropriately determined, and for example, the line width (dimension in the direction orthogonal to the direction surrounding the cell 55) 54W can be about 0.6 to 8.0 mm. In the case of forming the bonded portions 54 in a dotted line (intermittently in the direction surrounding the cells 55), it is preferable that the length 54L of the bonded portion 54 in the direction surrounding the cell 55 is about 0.6 to 8.0 mm, and the interval 54D between the two adjacent bonded portions is about 0.8 to 10.0 mm. In particular, in the case of the strong bonded portion 54a, it is preferable that the line width 54W is about 1.0 to 4.0 mm, the length 54L of the bonded portion 54 is about 1.5 to 4.0 mm, and the point interval 54D is about 0.8 to 2.5 mm. Further, in the case of the weak bonded portion 54b, it is preferable that the line width 54W is about 0.6 to 3.5 mm, the length 54L of the bonded portion 54 is about 0.6 to 2.5 mm, and the point interval 54D is about 1.0 to 4.0 mm The width of the bonded portion 54 in the case where the bonded portions 54 are formed in a continuous linear shape, and the line width 54W in the case where the bonded portions 54 are formed in a dotted line shape are constant in the direction surrounding the cell 55 and also can be changed. In addition, in the case where the bonded portions 54 are formed in a dotted line shape, the shape of each bonded portion 54 can be appropriately determined, and all of the bonded portions may have the same shape, or the bonded portions have different shapes depending on the site. In particular, it is preferable to provide the bonded portion 54 at least at one of the intermediate position and each vertex position in each cell 55. Further, in the case of the strong bonded portion 54a, it is preferable to provide it at each vertex position, but in the case of the weak bonded portion 54b, it is preferable not to provide the weak bonded portion 54b, because the weak bonded portion 54b can be peeled off easily if not provided at each vertex position, and the cells 55 are smoothly coalesced. In the case where the bonded portion 54 is provided at each vertex position, it is desirable that the bonded portion 54 have a radial (star) shape protruding in the direction of each side.

Figure 15:
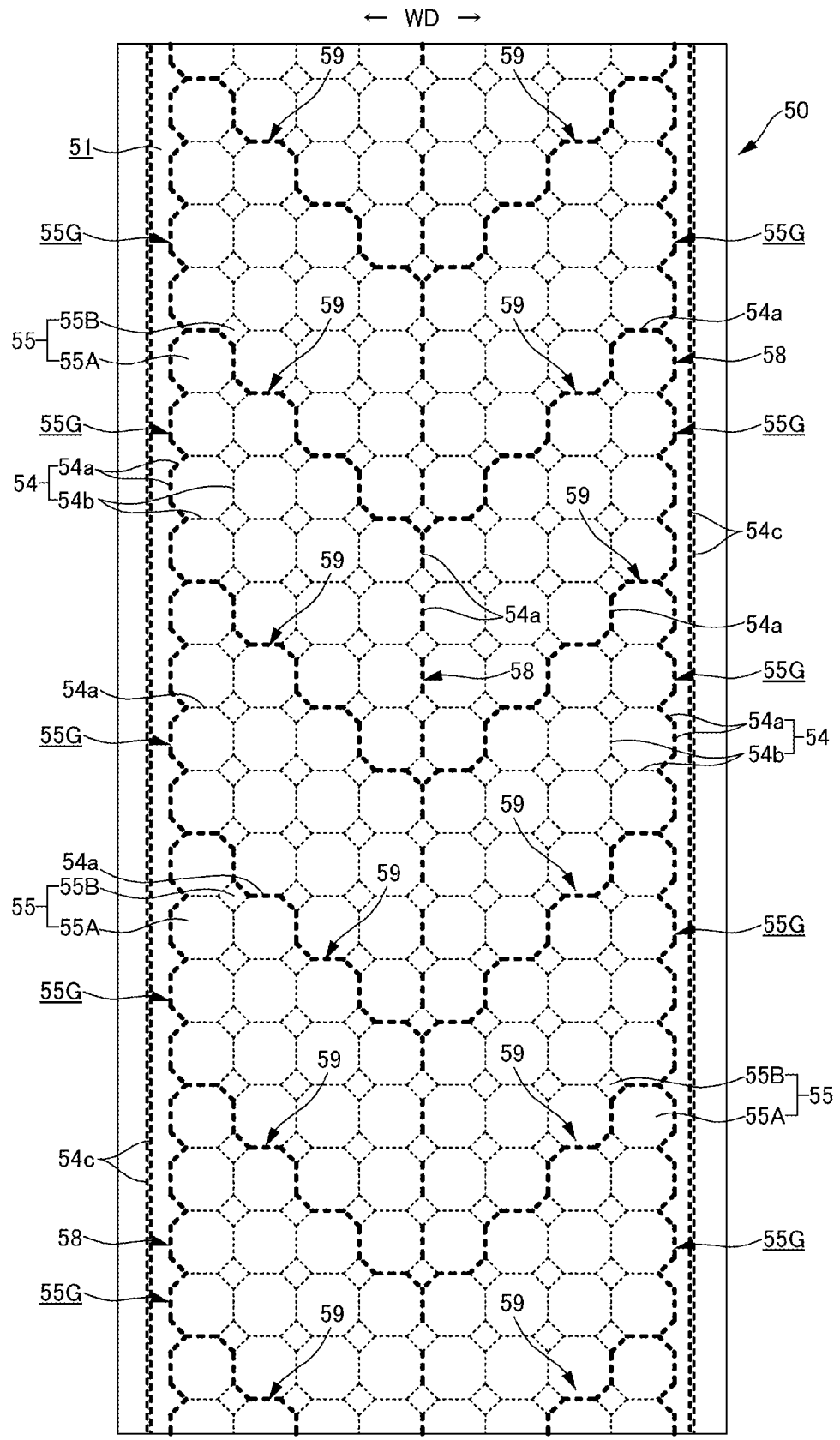
FIG. 15 is a plan view of an absorber illustrating bonded portions in a simplified manner.
Figure 16:
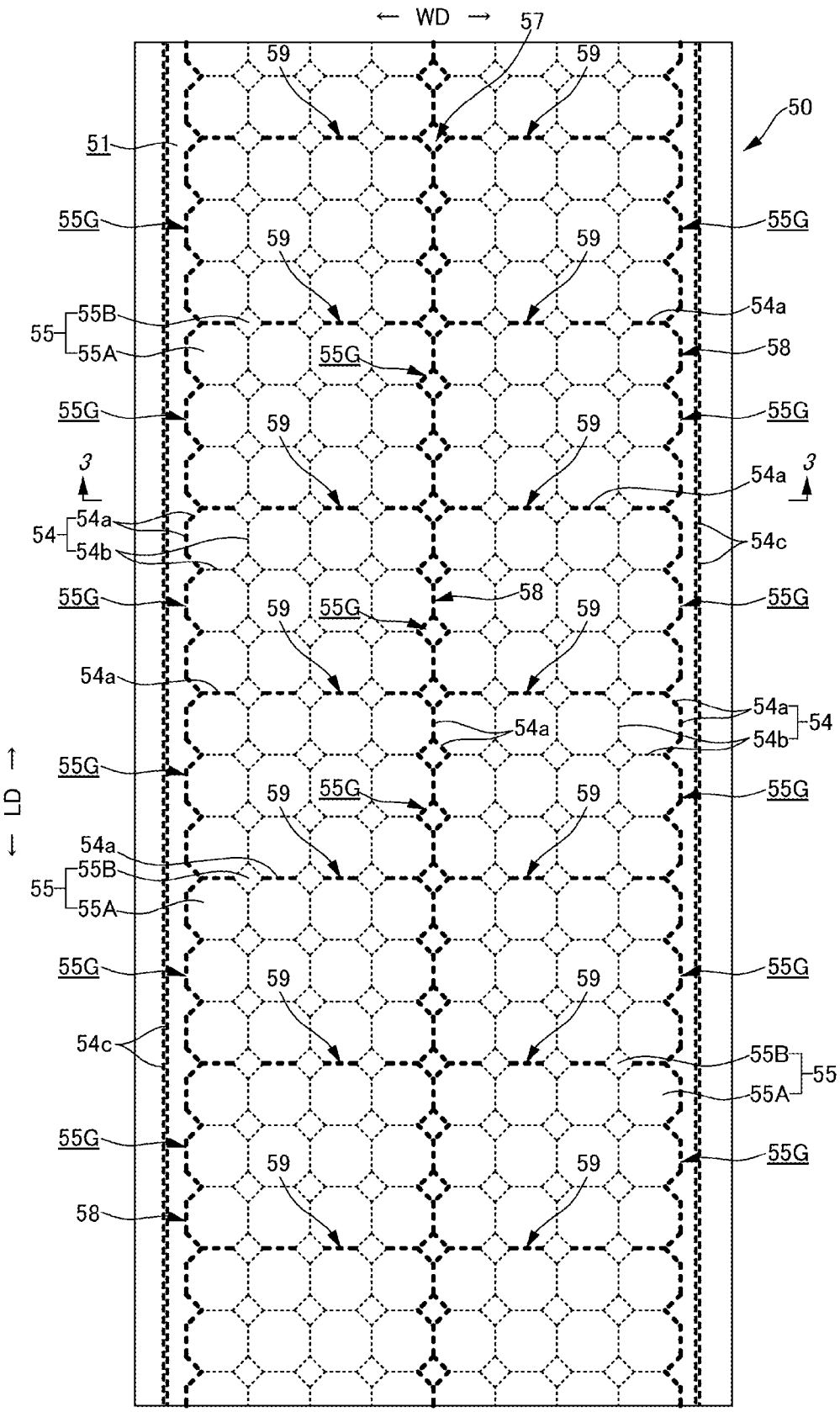
FIG. 16 is a plan view of an absorber illustrating bonded portions in a simplified manner.

The size, shape, arrangement (that is, arrangement of the strong bonded portion 54a) of the maximum enlargement section 55G can be appropriately determined, but if the maximum enlargement section 55G is too small, it becomes insignificant to provide the strong bonded portion 54a, and even if a large number of the cells 55 are provided, when the maximum enlargement is formed to be elongated, after the cells 55 are coalesced, the maximum enlargement section becomes to have a shape in which it is difficult for the cells to be swollen. Therefore, it is preferable that, as illustrated in FIGS. 8, 15, and 16, the each of the maximum enlargement sections 55G surround a portion where three or more octagonal cells 55A and four or more diamond-shaped cells 55B are arranged without any space in the front-back direction LD and the width direction WD. As a result, the cells 55 are successively coalesced and smoothly enlarged to the maximum enlargement section 55G, and the maximum enlargement section 55G has a shape that is easy to be swollen. When the cells 55 are enlarged to the maximum enlargement section 55G, the increase in the volume of the cells 55 relative to the number of the coalesced cells 55 becomes excellent. In FIGS. 11 to 16, as indicated by reference signs, the strong bonded portions 54a or the weak bonded portions 54b having a relatively high bonding strength are represented by bold dotted lines, and the weak bonded portions 54b having relatively weak bonding strength are represented by thin dotted lines.

A portion where the continuous three sides of one octagonal cell 55A and one side of a diamond shape following the three sides are connected can be a linear portion in the front-back direction LD, the width direction WD, and the oblique direction, and the portion where continuous five sides in one octagonal cell 55A can be a 90° corner portion (direction turning portion). Further, a portion where the bonded portions 54 along the front-back direction LD and the width direction WD of the octagonal cell 55A are continued can also be a linear portion of the peripheral edge of the maximum enlargement section 55G. Therefore, by combining these linear portions and corner portions, the peripheral edge shape (arrangement of the strong bonded portions 54a) of the maximum enlargement section 55G can be formed into a substantially triangular shape as illustrated in FIG. 8, a substantially parallelogram shape as illustrated in FIG. 15, or a substantially quadrangular shape as illustrated in FIG. 16.

Figure 17:
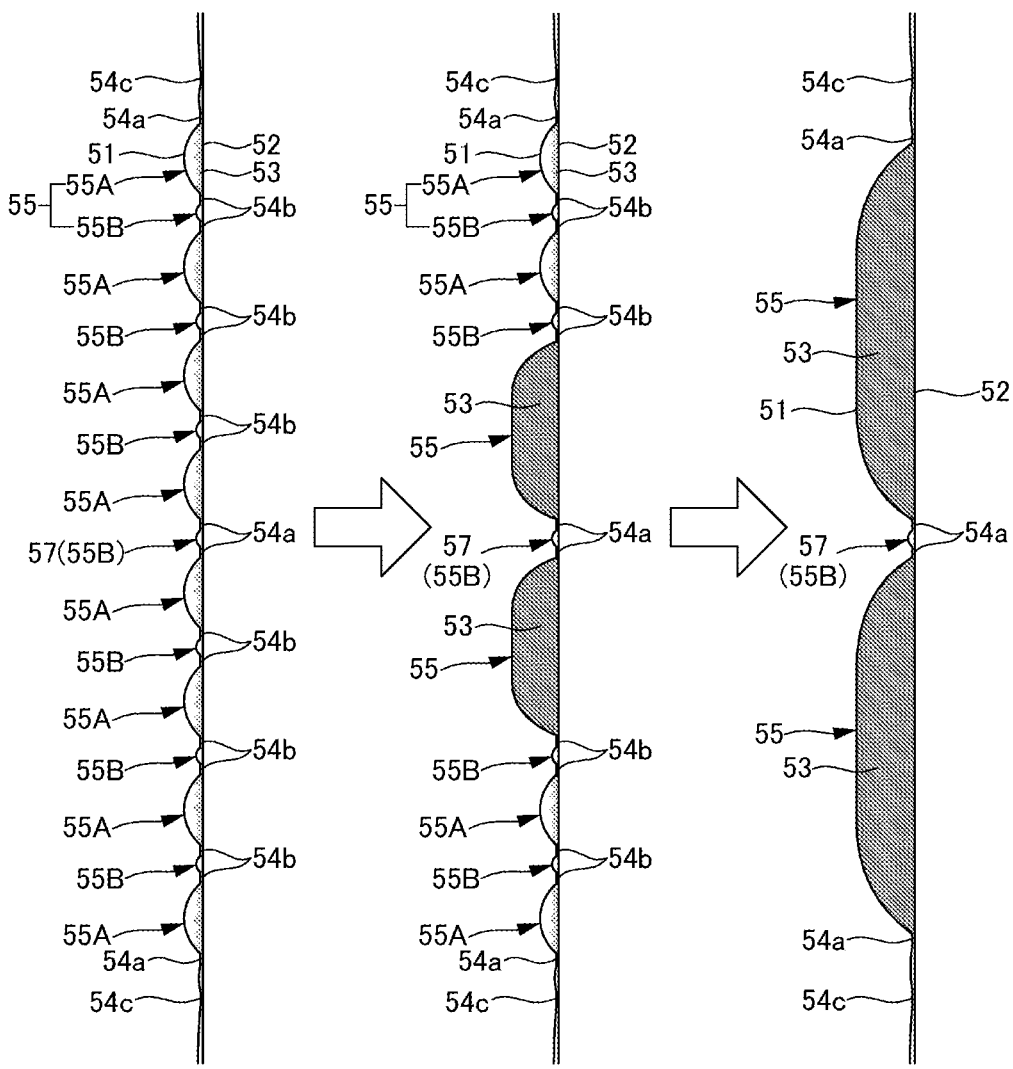
FIG. 17 is a cross-sectional view taken along line 3-3 in FIG. 16.

As illustrated in FIGS. 8 and 15, all of the maximum enlargement sections 55G may satisfy the above conditions (a shape surrounding a portion where three or more octagonal cells 55A and four or more diamond-shaped cells 55B are arranged without space in the front-back direction and the width direction WD) or only some of the maximum enlargement sections 55G may satisfy the above conditions as illustrated in FIG. 16. For example, one preferred embodiment is that, as illustrated in FIG. 16, at the center of the width direction WD of the absorber 50, at least one low-swelling-cell row 57, in which all of the bonded portions 54 on the both side edges on a row of the diamond-shaped cells 55 arranged linearly in the front-back direction are the strong bonded portions 54a, is provided, and cell portions on the both sides in the width direction WD of the low-swelling-cell row 57 have a higher swellable height than the low-swelling-cell row 57. The low-swelling-cell row 57 is a row of the cells 55 in which both side edges are comprised of the strong bonded portions 54a and which are arranged linearly in the front-back direction, and the low-swelling-cell row 57 is a portion in which the maximum volume is small and the height can be kept low even if the inside superabsorbent polymer particles 53 are swollen. When the portions having a higher swellable height than the low-swelling-cell row 57 are provided on the both sides in the width direction WD of such low-swelling-cell row 57, as illustrated in FIG. 17, a groove having the low-swelling-cell row 57 as the bottom is formed after absorption, and therefore the liquid diffusibility in the front-back direction along the groove improves. A plurality of low-swelling-cell rows 57 can be provided adjacent to or spaced apart from each other in the width direction WD of the absorber 50.

It is preferable that the low-swelling-cell row 57 does not contain a superabsorbent polymer particle 53 or contains a smaller amount of the superabsorbent polymers 53 per unit area than the cells 55 on the both sides in the width direction WD of the low-swelling-cell row (for example, a ratio of the basis weight is ½ or less, especially ¹/₁₀ or less). By reducing the amount of the contained superabsorbent polymer particles 53 in this manner, it is possible to form a liquid diffusion groove having a low bottom even upon the absorption. In addition, the inside of the low-swelling-cell row 57 does not give a hard texture due to the swelling pressure upon the absorption.

Although the arrangement of the strong bonded portion 54a is not particularly limited, for example, as indicated in the illustrated embodiment, if the strong bonded portions 54a continue throughout a certain range in a specific direction, such as the front-back direction LD, the width direction WD, and the oblique direction, the cells 55 on the both sides thereof are swollen due to absorption by the internal superabsorbent polymer particles 53, the strong bonded portions 54a are however not peeled off to the end. Therefore, after the absorption, the grooves with the bottom portions of the strong bonded portions 54a are formed along the specific directions, and the liquid diffusibility in the directions along the grooves is improved. In addition, if the strong bonded portions 54a continue in the width direction WD or in the oblique direction, it is possible to prevent the uneven distribution which would be caused by the movement of the gelled superabsorbent polymer particles 53 swollen upon the absorption as well as to improve the liquid diffusibility in the direction. Further, when the bonded portions positioned on the outermost side in the width direction WD are peeled off, there is a possibility that the superabsorbent polymer particles 53 or the gelled superabsorbent polymer particles leak to the outside of the absorber 50, and therefore it is desirable that the bonded portions are the strong bonded portions 54a. From the same viewpoint, it is preferable that the front surface side sheet 51 and the back surface side sheet 52 are extended to the outside in the width direction WD to some extent beyond the region where the cells 55 are formed, and the edge bonded portions 54c are provided in the extended portions for the reinforcement.

For example, one preferable embodiment is that, as illustrated in FIGS. 8, 15, and 16, the longitudinal-strong-bond lines 58, in each of which the strong bonded portions 54a are continuously aligned in the front-back direction along the maximum length of the absorber 50, are provided in the center portion and the both side portions in the width direction WD of the absorber 50. A plurality of the lateral-strong-bond lines 59, in each of which the strong bonded portions 54a are aligned in the width direction WD or the oblique direction from the longitudinal-strong-bond line 58 in the center portion to each of the longitudinal-strong-bond lines 58 in the both side portions, is provided at intervals in the front-back direction. In this embodiment, the liquid diffusibility in the longitudinal direction is improved by the longitudinal-strong-bond lines 58, and the liquid diffusibility in the lateral direction is improved by the lateral-strong-bond lines 59. In addition, the longitudinal-strong-bond lines 58 in both side portions also have a function of preventing leakage of the superabsorbent polymer particles 53 from the both side edges.

In particular, as illustrated in FIG. 8, it is preferable that the lateral-strong-bond lines 59 are formed in a zigzag shape extending in the front-back direction while repeatedly bending left and right between the longitudinal-strong-bond line 58 in the center portion and each of the longitudinal-strong-bond lines 58 in the both side portions. As a result, the maximum enlargement section 55G having a substantially triangular shape with one of vertexes positioned in the longitudinal-strong-bond line 58 in the center portion and the maximum enlargement section 55G having a substantially triangular shape with one of the vertexes positioned in each of the longitudinal-strong-bond lines 58 on the both side portions are repeatedly formed alternately in the front-back direction. When the lateral-strong-bond lines 59 are formed in the zigzag shape as described above, it is preferable because the liquid diffusion in the lateral direction can be efficiently facilitated with the small number of the lateral-strong-bond lines 59, and the maximum enlargement section 55G has a substantially triangular shape which is easily swollen, and the increase in the volume of the cells 55 relative to the number of the coalesced cells 55 is excellent.

Although not illustrated, it is also possible to omit the longitudinal-strong-bond line in the center portion and only provide the lateral-strong-bond lines 59.

The number of the longitudinal-strong-bond lines 58 and the number of the lateral-strong-bond lines 59 may be suitably determined, but three to four longitudinal-strong-bond lines 58 are preferably provided when the longitudinal-strong-bond line is provided along the side edge of the cells 55 positioned on the outermost side of the absorber in the width direction WD, and one to two longitudinal-strong-bond lines 58 are provided when the longitudinal-strong-bond line is not provided along the side edge. It is desirable that the number of the lateral-strong-bond lines 59 be about four to ten.

As illustrated in FIG. 8, it is also possible to provide the empty cells 56 which do not contain the superabsorbent polymer particles 53 or which contain a smaller amount of the superabsorbent polymer particles 53 than other cells even if the cells contain them. In FIG. 8, an area 53A having a pattern of hatched lines indicates a region for containing the superabsorbent polymer particles 53. Since this region is based on assumption of the shape of a region in which the superabsorbent polymer particles 53 are dispersed in manufacturing, there are portions which are not covered by the pattern of the hatched lines in the cells 55 in the peripheral edge, in the case where the superabsorbent polymer particles 53 can move in the cell 55, the position of the superabsorbent polymer particle 53 in the cell 55 is not fixed in a product, and the superabsorbent polymer particles 53 can be distributed throughout the cell 55 in the same manner as in the state illustrated in FIG. 7. The amount of the superabsorbent polymer particles 53 contained in the empty cell 56 is preferably ½ or less, particularly ¹/₁₀ or less, of the other cells in terms of weight ratio, and it is particularly preferable that the superabsorbent polymer particles 53 are not contained at all. For example, since the front end and the back end of the absorber 50 are formed by cutting into individual absorbers 50 at the time of manufacture, if the superabsorbent polymer particles 53 are included at this position, the life of a blade of a cutting device may be shortened. Therefore, it is desirable that at least the cell 55 at the position through which the front and back ends of the absorber 50 pass be the empty cell 56. Further, in the absorber 50 obtained by mixing superabsorbent polymer particles 53 with hydrophilic short fibers such as fluff pulp and being accumulating them in a cotton form, generally the intermediate portion of the front-back direction LD is formed in a shape narrowed along the legs. However, even in the absorber 50, by making the cells 55 on both sides in the middle in the front-back direction LD the empty cells 56, this portion becomes less swellable even after absorption, and therefore, the absorber 50 fits around the legs even after absorption.

In the case of manufacturing the absorber 50, it is difficult to accurately distribute a predetermined amount of the superabsorbent polymer particles 53 to individual cells 55. Therefore, it is preferable to combine the front surface side sheet 51 and the back surface side sheet 52 as one unit by forming the bonded portion 54 and to confine the superabsorbent polymer particles 53 in the cell 55 after the superabsorbent polymer particles 53 are uniformly distributed over the entire region (the region excluding the part to be the empty cell 56) of the region containing the superabsorbent polymer particles 53 on the front surface side sheet 51 or the back surface side sheet 52. In this case, it is difficult to spray the superabsorbent polymer particles 53 with an accurate shape matching the peripheral edges of the cell 55, particularly with respect to the peripheral cells 55 positioned at the peripheral edges of the region containing the superabsorbent polymer particles 53. Therefore, it is desirable that, as can be seen from the shape of the scattering region 53A of the superabsorbent polymer particles 53 indicated by oblique lines in FIG. 8, the superabsorbent polymer particles 53 be sprayed such that the peripheral edges of the scattering region 53A passes through the middle of the peripheral cells 55. In this case, the amount of the superabsorbent polymer particles 53 contained in the peripheral cells 55 is less than the cell 55 positioned inside the peripheral cell 55, and in the case where the cell 55 is provided outside the peripheral cell 55, this outer cell 55 is the empty cell 56 substantially containing no superabsorbent polymer particles 53.

In the above example, only the superabsorbent polymer particles 53 are contained in the cell 55, but it is also possible to contain the superabsorbent polymer particles 53 together with particulate materials other than the superabsorbent polymer particles 53, such as deodorant particles.

Explanation of Terms Used Herein

In the case where the following terms are used in the specification, those have the following meanings unless otherwise specified in the specification.

"Machine direction" and "cross direction" mean the flow direction (MD) in manufacturing equipment and the lateral direction (CD) orthogonal to the flow direction, and either one is the front-back direction of a product, and the other is the width direction of a product. The MD of a nonwoven fabric is the direction of fiber orientation of the nonwoven fabric. "Fiber orientation" is a direction along which a fiber of a nonwoven fabric runs and determined by, for example, a measurement method in accordance with the fiber orientation test method based on the zero distance tensile strength of TAPPI standard method T481 and a simple measurement method for determining the fiber orientation direction from the tensile strength ratio in the front-back direction and the width direction.

"Spread state" means a flatly spread state without shrinkage or slackness.

"Stretch rate" means the value when the natural length is taken as 100%.

"Artificial urine" is prepared by mixing urea: 2 wt %, sodium chloride: 0.8 wt %, calcium chloride dihydrate: 0.03 wt %, magnesium sulfate heptahydrate: 0.08 wt %, and ion exchanged water: 97.09 wt %, and those are used at a temperature of 40° C. unless otherwise specified.

"Gel strength" is measured as follows: Add 1.0 g of superabsorbent polymer to 49.0 g of artificial urine and stir with a stirrer. After leaving generated gel for three hours in a thermohygrostat bath at 40° C.×60% RH, return to room temperature, and measure the gel strength with Curdmeter (MAX ME-500, manufactured by I. techno Engineering).

"Basis weight" is measured as follows. After preliminary drying a sample or a test piece, the sample or the test piece is left in a test chamber or equipment in the standard state (the test location is at a temperature of 20±5° C. and with a relative humidity of 65% or less) to be constant weight. The preliminary drying refers to making a sample or a test piece constant weight in an environment not exceeding a temperature of 50° C. and a relative humidity of 10 to 25%. For fibers with an official moisture regain of 0.0%, preliminary drying may not be performed. A sample of dimensions 200 mm×250 mm (±2 mm) is cut using a cutting template (200 mm×250 mm, ±2 mm) from a test piece in a constant weight. The basis weight is set by weighing the sample, multiplying by twenty, and calculating the weight per one square meter.

"Thickness" is automatically measured under the conditions of a load of 10 gf/cm$^2$ and a pressing area of 2 cm$^2$ using an automatic thickness measuring device (KES-G5 handy compression testing machine).

"Water absorption" is measured according to JIS K7223-1996 "Test method for water absorption of super absorbent resin".

"Water absorption rate" is the "time to end point" when JIS K7224-1996 "Test method for water absorption rate of super absorbent resin" has been carried out using 2 g of superabsorbent polymer and 50 g of physiological saline solution.

When environmental conditions in tests and measurements are not described, the tests and measurements shall be carried out in a test room or apparatus in a standard state (a temperature of 20±5° C. and a relative humidity of 65% or less at the test location).

The dimension of each part means the dimension in the spread state, not the natural length state, unless otherwise stated.

REFERENCE SIGNS LIST 11 liquid impervious sheet
12 outer sheet
12T target sheet
13 fastening tape
13A engagement portion
13B tape main unit section
13C tape attachment part
30 top sheet
40 intermediate sheet
60 three-dimensional side gather
62 gather sheet
50 absorber 51 front surface side sheet
51c recess
52 back surface side sheet
53 superabsorbent polymer particles
54 bonded portion
54a strong bonded portion
54b weak bonded portion
54c edge bonded portion
54e first bonded portion
54f second bonded portion
55 cell
55A octagonal cell
55B diamond-shaped cell
55G maximum enlargement section
56 empty cell
57 low-swelling-cell row
58 longitudinal strong bond line
59 lateral strong bond line
LD front-back direction
WD width direction

The invention claimed is:

1. An absorbent article comprising an absorber having a front surface side and a back surface side, the absorber including:
 a front surface side sheet;
 a back surface side sheet disposed on the back surface side of the front surface side sheet;
 a plurality of cells each of which is surrounded by bonded portions of the front surface side sheet and the back surface side sheet and inside each of which the front surface side sheet and the back surface side sheet are not bonded; and
 particulate materials which include superabsorbent polymer particles and which are contained in each of the cells,
 wherein the bonded portions are provided in continuous line shapes or dotted line shapes so as to form a pattern of same-sized octagons arranged without space in both a front-back direction and a width direction, wherein the width direction is orthogonal to the front-back direction;
 wherein the pattern of same-sized octagons are arranged such that all interior angles of the octagons are 135°, and lengths of two pairs of opposite sides of the octagons whose facing directions are mutually orthogonal are equal;
 wherein the pattern of same-sized octagons define diamond-shaped cells between the plurality of cells, and lengths of all sides of each diamond-shaped cell being equal;
 wherein the bonded portions comprise strong bonded portions and weak bonded portions, and wherein at least two continuous sides in each of the octagons are weak bonded portions which can be peeled off due to a swelling force of the superabsorbent polymer particles in the cells adjacent to the bonded portions;
 wherein strong bonded portions provided in a center portion and side portions on either side of the center portion along the width direction are longitudinal strong-bond lines, each of the longitudinal strong-bond lines continuously extending in the front-back direction;
 wherein strong bonded portions provided in a zigzag shape bending left and right between the longitudinal-strong-bond line in the center portion and each of the longitudinal-strong-bond lines in the side portions are lateral-strong-bond lines; and
 wherein the longitudinal-strong-bond lines and the lateral-strong-bond lines define maximum enlargement sections, each of the maximum enlargement sections having a substantially triangular shape.

2. The absorbent article according to claim 1,
 wherein the diamond-shaped cells do not contain a superabsorbent polymer particle or contain a smaller amount of the superabsorbent polymer particles per unit area than the plurality of cells.

3. The absorbent article according to claim 1,
 wherein the weak bonded portions comprise first bonded portions and second bonded portions, the first bonded portions positioned on sides parallel to the front-back direction and the width direction having lower bonding strength than the second bonded portions positioned on sides parallel to an oblique direction that is situated at an angle relative to the front-back direction and the width direction.

4. The absorbent article according to claim 1,
 wherein the weak bonded portions comprise first bonded portions and second bonded portions, the first bonded portions positioned on sides parallel to the front-back direction and the width direction having higher bonding strength than the second bonded portions positioned on sides parallel to an oblique direction that is situated at an angle relative to the front-back direction and the width direction.

5. The absorbent article according to claim 1, wherein:
 each maximum enlargement section comprises three or more cells and four or more diamond-shaped cells that are arranged respectively without any space in the front-back direction and the width direction wherein the three or more cells and the four or more diamond-shaped cells are surrounded by strong bonded portions which are not peeled off against the swelling force of the superabsorbent polymer particles in adjacent cells; and
 wherein the bonded portions positioned inside the strong bonded portions in the maximum enlargement sections are the weak bonded portions.

6. The absorbent article according to claim 5,
 wherein the bonded portions are portions where the front surface side sheet and the back surface side sheet are welded;
 wherein the weak bonded portions and the strong bonded portions are provided in dotted line patterns;
 wherein a line width of the weak bonded portions is narrower than a line width of the strong bonded portions; and
 wherein a point interval of the weak bonded portions is wider than a point interval of the strong bonded portions.

7. The absorbent article according to claim 1,
 wherein bonded portions are not provided at vertex positions where sides of the cells on which the weak bonded portions are positioned intersect with each other.

8. The absorbent article according to claim 1,
 wherein at least cells provided at positions through which front and back ends of the absorber pass and cells in the side portions in an intermediate portion of the front-back direction of the absorber are empty cells which do not contain a superabsorbent polymer particle or which contain a smaller amount of the superabsorbent polymer particles per unit area than other cells.

9. The absorbent article according to claim 2,
 wherein the weak bonded portions comprise first bonded portions and second bonded portions, the first bonded portions positioned on sides parallel to the front-back direction and the width direction having lower bonding strength than the second bonded portions positioned on sides parallel to an oblique direction that is situated at an angle relative to the front-back direction and the width direction.

10. The absorbent article according to claim 2,
wherein the weak bonded portions comprise first bonded portions and second bonded portions, the first bonded portions positioned on sides parallel to the front-back direction and the width direction having higher bonding strength than the second bonded portions positioned on sides parallel to an oblique direction that is situated at an angle relative to the front-back direction and the width direction.

11. The absorbent article according to claim 2, wherein:
each maximum enlargement section comprises three or more cells and four or more diamond-shaped cells that are arranged respectively without any space in the front-back direction and the width direction, wherein the three or more cells and the four or more diamond-shaped cells are surrounded by strong bonded portions which are not peeled off against the swelling force of the superabsorbent polymer particles in adjacent cells; and
wherein the bonded portions positioned inside the strong bonded portions in the maximum enlargement sections are the weak bonded portions.

12. The absorbent article according to claim 1,
wherein the bonded portions are portions where the front surface side sheet and the back surface side sheet are welded;
wherein the weak bonded portions and the strong bonded portions are provided in dotted line patterns;
wherein a line width of the weak bonded portions is narrower than a line width of the strong bonded portions; and
wherein a point interval of the weak bonded portions is wider than a point interval of the strong bonded portions.

* * * * *